(12) United States Patent
Kato et al.

(10) Patent No.: US 9,782,197 B2
(45) Date of Patent: Oct. 10, 2017

(54) TISSUE GRASPING DEVICE

(71) Applicant: OLYMPUS CORPORATION, Hachioji-shi, Tokyo (JP)

(72) Inventors: Satoko Kato, Tokyo (JP); Takayasu Mikkaichi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/264,435

(22) Filed: Sep. 13, 2016

(65) Prior Publication Data
US 2017/0000509 A1 Jan. 5, 2017

Related U.S. Application Data

(63) Continuation of application No. PCT/JP2015/064040, filed on May 15, 2015.

(30) Foreign Application Priority Data

Aug. 22, 2014 (JP) .................................. 2014-169610

(51) Int. Cl.
*A61B 17/26* (2006.01)
*A61B 17/3205* (2006.01)
(Continued)

(52) U.S. Cl.
CPC .. *A61B 17/32056* (2013.01); *A61B 17/22031* (2013.01); *A61B 17/29* (2013.01);
(Continued)

(58) Field of Classification Search
CPC ........ A61B 17/32056; A61B 17/22031; A61B 17/29; A61B 17/320016;
(Continued)

(56) References Cited

U.S. PATENT DOCUMENTS 5,108,406 A 4/1992 Lee
5,171,314 A 12/1992 Dulebohn
(Continued)

FOREIGN PATENT DOCUMENTS

JP H08-038497 A 2/1996
JP 2000-051229 A 2/2000
(Continued)

OTHER PUBLICATIONS

Jul. 21, 2015 International Search Report issued in International Patent Application No. PCT/JP2015/064040.
(Continued)

*Primary Examiner* — Ashley Fishback
(74) *Attorney, Agent, or Firm* — Oliff PLC

(57) ABSTRACT

A tissue grasping device includes a longitudinal axis member; an actuating member provided at a distal end portion of the longitudinal axis member; a wire member elongated to an outside of the actuating member and being curved in a loop shape; a through hole formed in a distal end surface of the actuating member and holding a first end side of the wire member such that the first end side of the wire member is capable of moving with respect to the actuating member; and a direction restriction portion provided at a side surface of the actuating member and fixing a second end portion of the wire member to the actuating member such that an elongated direction of a second end side of the wire member is coincide with a direction intersecting a side surface of the actuating member.

14 Claims, 20 Drawing Sheets

(51) Int. Cl.
*A61B 17/32* (2006.01)
*A61B 17/22* (2006.01)
*A61B 17/29* (2006.01)
*A61B 17/00* (2006.01)

(52) U.S. Cl.
CPC ............. *A61B 17/320016* (2013.01); *A61B 2017/00358* (2013.01); *A61B 2017/00818* (2013.01); *A61B 2017/2926* (2013.01); *A61B 2017/320064* (2013.01)

(58) Field of Classification Search
CPC  A61B 2017/00358; A61B 2017/00818; A61B 2017/2926; A61B 2017/320064
See application file for complete search history.

(56) References Cited

U.S. PATENT DOCUMENTS

| | | | |
|---|---|---|---|
| 5,514,156 | A | 5/1996 | Schulze et al. |
| 5,562,678 | A | 10/1996 | Booker |
| 6,440,062 | B1 | 8/2002 | Ouchi |
| 8,092,470 | B2 | 1/2012 | Miyamoto et al. |
| 9,039,721 | B2 | 5/2015 | Ziniti et al. |
| 2003/0023237 | A1* | 1/2003 | Mollenauer .......... A61B 18/085 606/27 |
| 2003/0187457 | A1 | 10/2003 | Weber |
| 2004/0059345 | A1 | 3/2004 | Nakao et al. |
| 2010/0243706 | A1 | 9/2010 | Cohen et al. |
| 2013/0006262 | A1 | 1/2013 | Lampropoulos et al. |
| 2013/0317515 | A1 | 11/2013 | Kuroda et al. |

FOREIGN PATENT DOCUMENTS

| | | |
|---|---|---|
| JP | 2005-160648 A | 6/2005 |
| JP | 2006-136726 A | 6/2006 |
| JP | 2006-517444 A | 7/2006 |
| JP | 2009-529983 A | 8/2009 |
| JP | 2010-240392 A | 10/2010 |
| JP | 4704518 B2 | 6/2011 |
| JP | 2012-101121 A | 5/2012 |
| NO | 2004/069025 A2 | 8/2004 |
| NO | 2007/106813 A2 | 9/2007 |
| WO | 94/04080 A1 | 3/1994 |
| WO | 2014/112438 A1 | 7/2014 |

OTHER PUBLICATIONS

Aug. 12, 2014 Office Action issued in Japanese Patent Application No. 2014-528357.
Feb. 25, 2014 International Search Report issued in International Patent Application No. PCT/JP2014/050310.
Jul. 13, 2016 Office Action issued in Chinese Patent Application No. 201480002432.4.
Oct. 15, 2015 Office Action issued in U.S. Appl. No. 14/305,553.

* cited by examiner

TISSUE GRASPING DEVICE

The application is a continuation application based on PCT Patent Application No. PCT/JP2015/064040, filed May 15, 2015, claiming priority based on Japanese Patent Application No. 2014-169610, filed Aug. 22, 2014, the contents of which are incorporated herein by reference.

FIELD OF THE INVENTION

The present invention relates to a tissue grasping device.

DESCRIPTION OF RELATED ART

As a method of treating infectious pancreatic necrosis, endoscopic necrosectomy is used. Endoscopic necrosectomy is a method in which an endoscope is used to approach lesions (pancreas) from the stomach, necrotic tissues are collected by a tissue grasping device, the tissue grasping device is moved into the stomach or to the outside of the body, and the necrotic tissues are removed from the tissue grasping device.

In the related art, a basket shaped forceps described in Japanese Patent No. 4704518 and the like are used as the tissue grasping device used for necrosectomy.

In the basket shaped forceps described in Japanese Patent No. 4704518, a treatment portion having four elastic wires is provided at a distal end side of a sheath. Proximal end portions of the four elastic wires are fixed to distal end portions of manipulation wires through a connecting member. The distal end portions of the four elastic wires are fixed to a distal end chip. The four elastic wires are disposed at equal angles around an axis line, and are curved to form a predetermined space within the four elastic wires. The basket shaped forceps configured in this manner capture a calculus in the treatment portion. When the manipulation wire is pulled, the treatment portion is reduced and the calculus is reliably retained in the treatment portion.

SUMMARY OF THE INVENTION

A tissue grasping device according to a first aspect of the present invention includes: a longitudinal axis member which is configured to be capable of inserting into a body; an actuating member provided at a distal end portion of the longitudinal axis member and configured to be capable of grasping a tissue; a wire member elongated to an outside of the actuating member and being curved in a loop shape; a through hole formed in a distal end surface of the actuating member and holding a first end side of the wire member such that the first end side of the wire member is capable of moving with respect to the actuating member; and a direction restriction portion provided at a side surface of the actuating member and fixing a second end portion of the wire member to the actuating member such that an elongated direction of a second end side of the wire member is coincide with a direction intersecting a side surface of the actuating member.

According to a second aspect of the present invention, in the tissue grasping device according to the first aspect, the actuating member may include: a first actuating member; and a second actuating member which is movable in a direction approaching to the first actuating member from a position relatively separated from the first actuating member. The wire member may include: a first wire member elongated to an outside of the first actuating member and being curved in a loop shape; and a second wire member elongated to an outside of the second actuating member and being curved in a loop shape. The through hole may include: a first through-hole holding a first end side of the first wire member such that the first end side of the first wire member is capable of moving with respect to the first actuating member; and a second through-hole holding a first end side of the second wire member such that the first end side of the second wire member is capable of moving with respect to the second actuating member. The direction restricting portion may include: a first direction restricting portion provided at a side surface of the first actuating member and fixing a second end portion of the first wire member to the actuating member such that an elongated direction of a second end side of the first wire member is coincide with a direction intersecting a side surface of the first actuating member; and a second direction restricting portion provided at a side surface of the second actuating member and fixing a second end portion of the second wire member to the actuating member such that an elongated direction of a second end side of the second wire member is coincide with a direction intersecting a side surface of the second actuating member.

According to a third aspect of the present invention, in the tissue grasping device according to the second aspect, the first end side of the first wire member may be supported by a distal end portion of the first actuating member, the second end side of the first wire member may be disposed at more proximal side than the first end side of the first wire member. The first end side of the second wire member may be supported by a distal end portion of the second actuating member, and the second end side of the second wire member may be disposed at more proximal side than the first end side of the second wire member.

According to a fourth aspect of the present invention, in the tissue grasping device according to the second aspect, the first direction restricting portion may support the second end side of the first wire member. The second direction restricting portion may support the second end side of the second wire member.

According to a fifth aspect of the present invention, in the tissue grasping device according to the fourth aspect, the first direction restricting portion may fix the second end side of the first wire member to the first actuating member. The second direction restricting portion may fix the second end side of the second wire member to the second actuating member.

According to a sixth aspect of the present invention, in the tissue grasping device according to the fourth aspect, the first direction restricting portion may be a third through-hole formed in the first actuating member and into which the second end side of the first wire member is inserted, and the second direction restricting portion may be a fourth through-hole formed in the second actuating member and into which the second end side of the second wire member is inserted.

According to a seventh aspect of the present invention, in the tissue grasping device according to the second aspect may further include a third wire member elongated to an outside of the first actuating member and being curved in a loop shape; and a fourth wire member elongated to an outside of the second actuating member and being curved in a loop shape.

According to an eighth aspect of the present invention, in the tissue grasping device according to the seventh aspect, the first end side of the first wire member may intersect a first end side of the third wire member, and the first end side of the second wire member may intersect a first end side of the fourth wire member.

According to a ninth aspect of the present invention, in the tissue grasping device according to the seventh aspect, the first end side of the first wire member and the first end side of the third wire member may be parallel, and a first end side of the second wire member and a first end side of the fourth wire member may be parallel.

DETAILED DESCRIPTION OF THE PREFERRED EMBODIMENTS

First Embodiment

Figure 1:
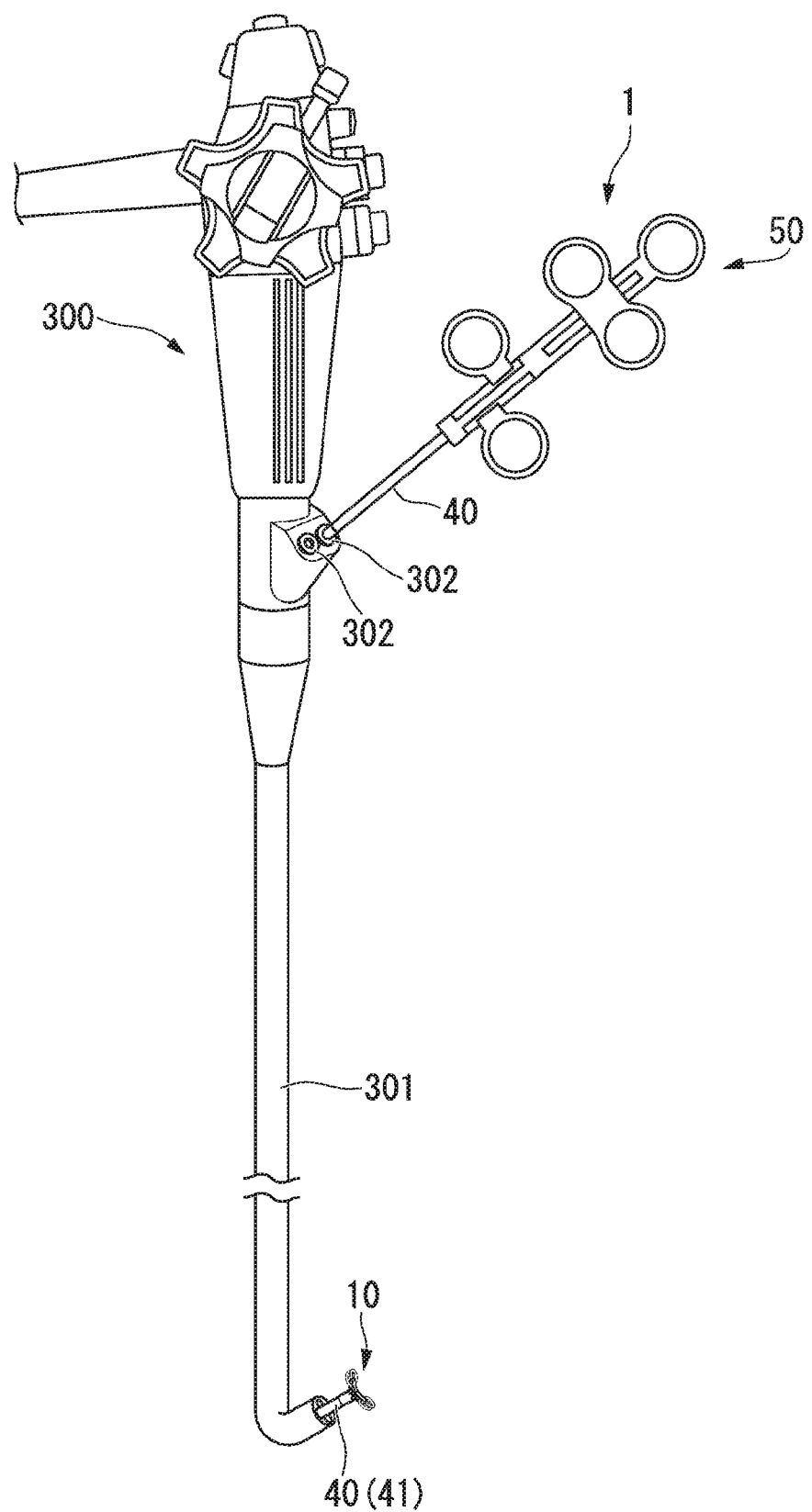
FIG. 1 is an overall view of a tissue grasping device of a first embodiment of the present invention and an endoscopic device used together with the tissue grasping device.

Hereinafter, a tissue grasping device according to a first embodiment of the present invention will be described with reference to FIG. 1 to FIG. 18. FIG. 1 is an overall view of a tissue grasping device 1 of the present embodiment and an endoscopic device 300 used together with the tissue grasping device 1.

A configuration of the endoscopic device 300 is not particularly limited. For example, in the present embodiment, the endoscopic device 300 is a flexible endoscope and includes a flexible endoscope insertion portion 301 which is inserted from the mouth to the stomach. A treatment tool channel 302 into which the tissue grasping device 1 is inserted is provided in the endoscope insertion portion 301.

The tissue grasping device 1 includes a treatment portion 10 that performs treatment in the body, an insertion portion 40 having a distal end portion at which the treatment portion 10 is provided, and a manipulation portion 50 that is provided at a proximal end portion of the insertion portion 40. Hereinafter, the treatment portion 10 side with respect to the manipulation portion 50 is referred to as a distal end side, and the manipulation portion 50 side with respect to the treatment portion 10 is referred to as a proximal end side.

Figure 2:
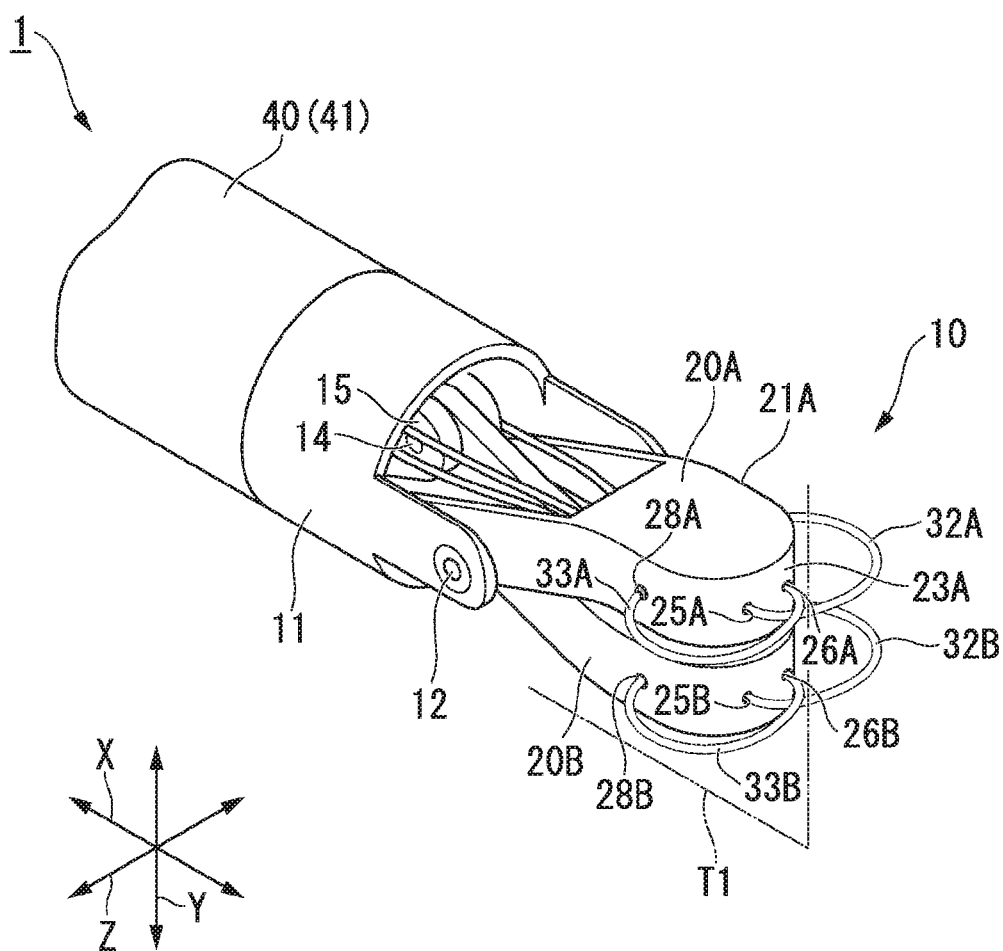
FIG. 2 is a perspective view of a treatment portion of the tissue grasping device.

As shown in FIG. 1 and FIG. 2, the insertion portion 40 is a member which is inserted into the treatment tool channel 302 of the endoscopic device 300 from a distal end. The insertion portion 40 includes a longitudinal axis member 41 extending along a first axis X in a natural state in which no external force is applied and being able to be inserted into the body. The longitudinal axis member 41 is a tubular member whose distal end side and proximal end side are opened. The longitudinal axis member 41 is flexible enough to advance and retract inside the treatment tool channel 302 even when the treatment tool channel 302 of the endoscopic device 300 is curved.

Figure 3:
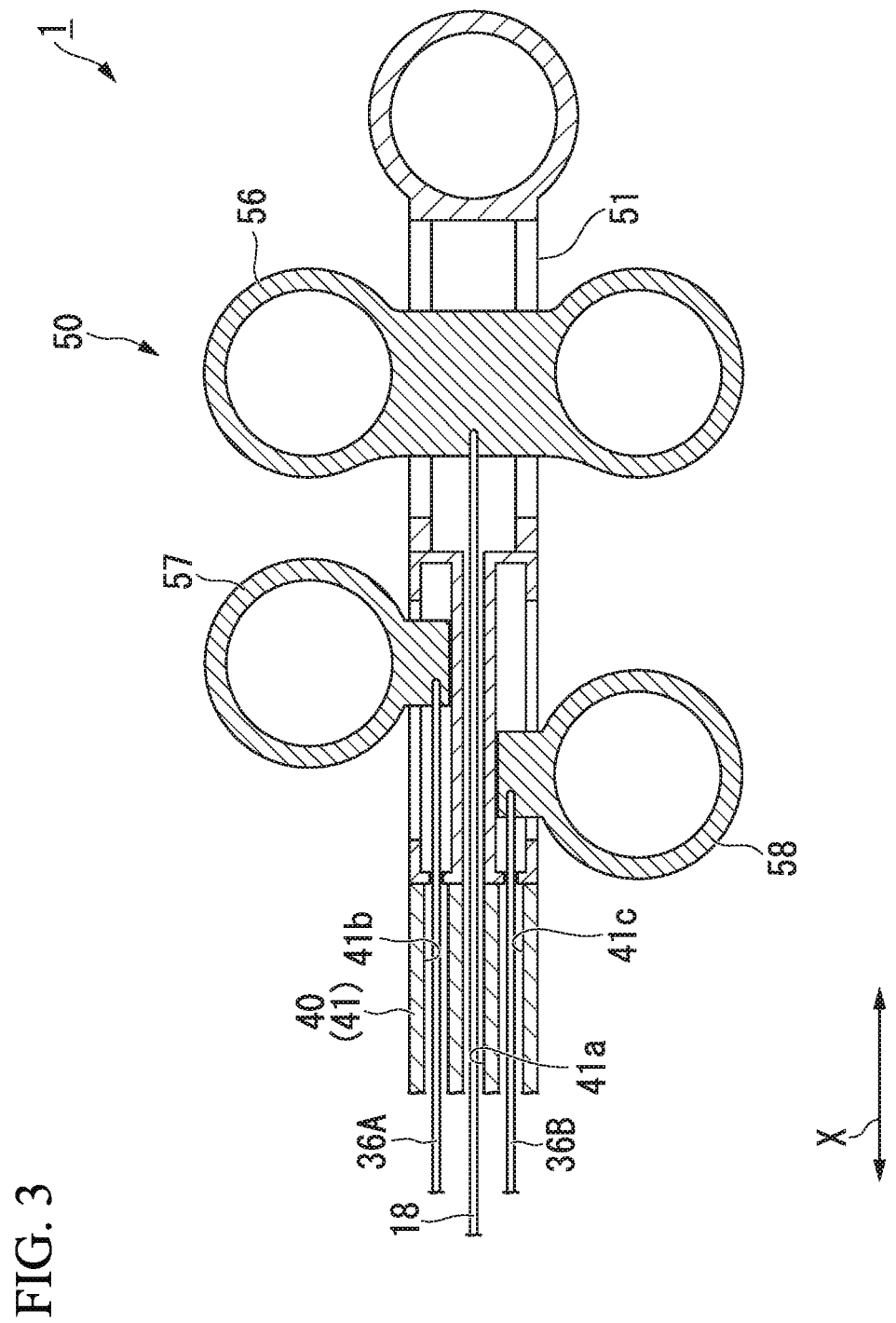
FIG. 3 is a cross-sectional view of an internal structure of a manipulation portion of the tissue grasping device.

As shown in FIG. 3, lumens 41$a$, 41$b$, and 41$c$ are formed in the longitudinal axis member 41. The three lumens 41$a$, 41$b$, and 41$c$ are disposed at, for example, parts that are positioned at vertices of a triangle inside a circular cross section perpendicular to the first axis X.

Figure 4:
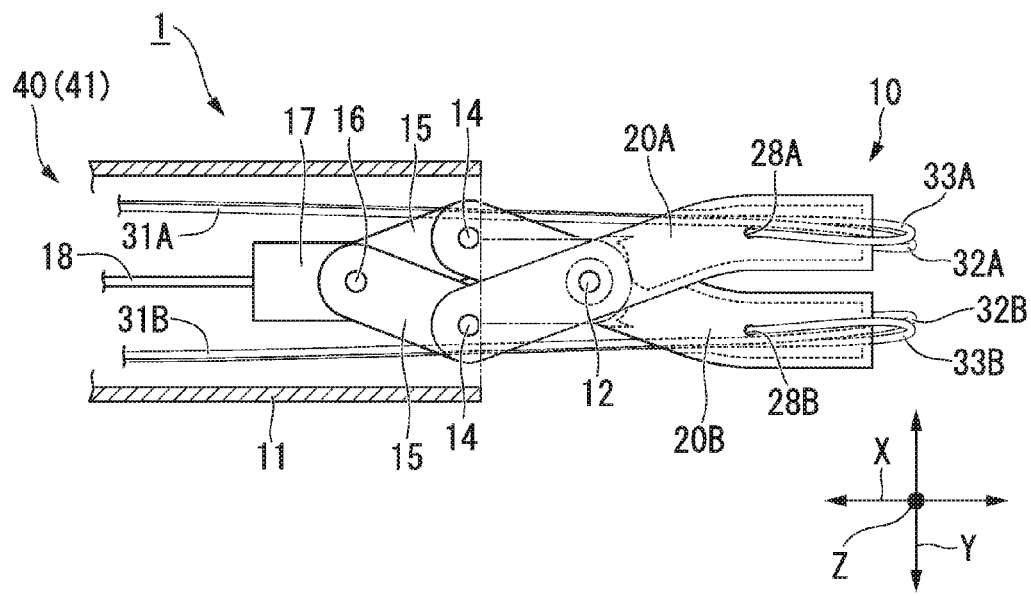
FIG. 4 is a side view including a partially cross-sectional view along an X-Z plane when an actuating member in a treatment portion of the tissue grasping device is in a closed state.

As shown in FIG. 2 and FIG. 4, the treatment portion 10 is provided at a distal end portion of the longitudinal axis member 41 of the insertion portion 40. The treatment portion 10 includes a tubular housing 11 fixed to a distal end of the longitudinal axis member 41 and a first actuating member 20A and a second actuating member 20B which are rotatably supported by the housing 11.

In the present embodiment, since the actuating members 20A and 20B have substantially the same configuration, the configuration of the first actuating member 20A is denoted with the letter "A" after the number, and the configuration corresponding to the second actuating member 20B is denoted with the letter "B" after the same number. Accordingly, some redundant descriptions will be omitted. Since loop portions 32A, 33A, 32B, and 33B, actuating members 90A and 90B, and the like, which will be described below, have substantially the same configuration, only different parts will be described.

Figure 5:
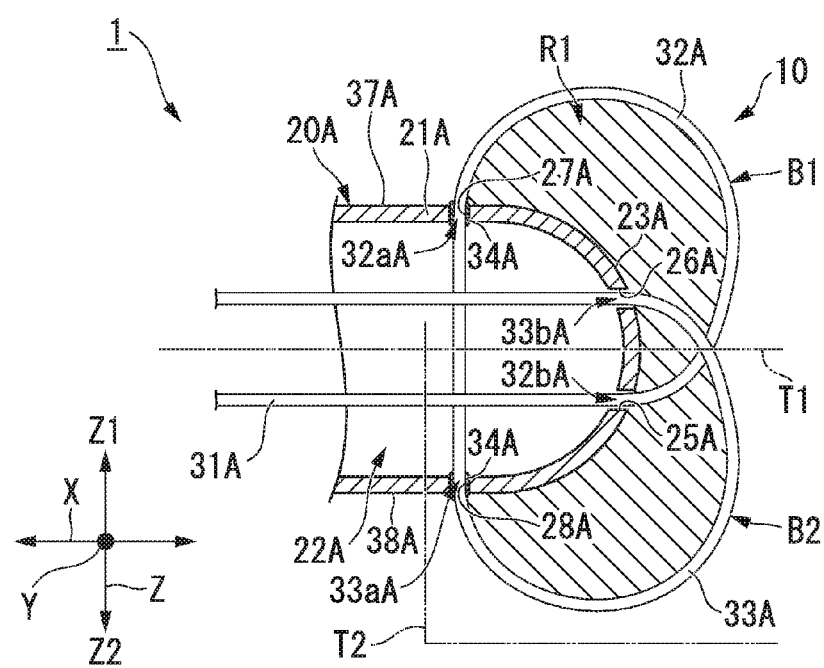
FIG. 5 is a cross-sectional view along an X-Z plane of a first actuating member of the treatment portion.

The first actuating member 20A extends along the first axis X. As shown in FIG. 2 and FIG. 5, an internal space 22A is formed in a wall portion 21A of the first actuating member 20A. A distal end surface 23A of the wall portion 21A is formed in a curved shape that is convex toward a distal side. Through-holes 25A, 26A, 27A, and 28A formed in the wall portion 21A will be described below in detail.

A hole (not shown) is formed in an intermediate portion along the first axis X of the first actuating member 20A. A fixing pin 12 (shown in FIG. 4) fixed to the housing 11 is inserted into the hole. First end portions of intermediate links 15 are rotatably coupled to each of proximal end sides of the actuating members 20A and 20B through a pin 14. A manipulation block 17 is rotatably coupled to the second end portions of the two intermediate links 15 through a pin 16. A distal end portion of an open-close manipulation wire (a manipulation member) 18 is coupled to the manipulation block 17. That is, the distal end portion of the open-close manipulation wire 18 is coupled to the actuating members 20A and 20B through the manipulation block 17 and the intermediate link 15.

Figure 6:
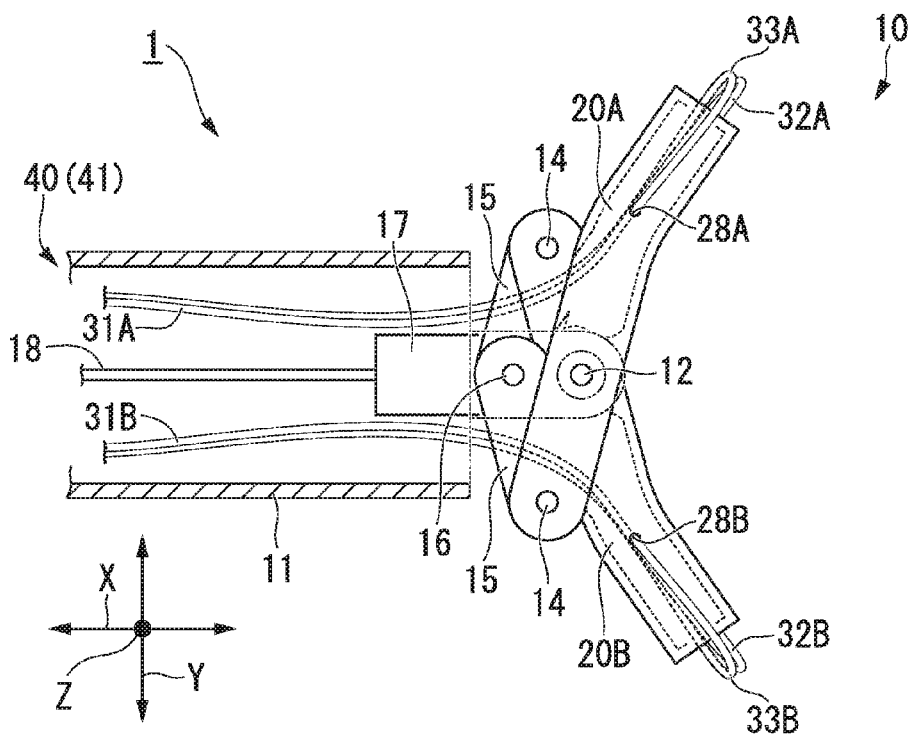
FIG. 6 is a side view including a partially cross-sectional view along an X-Z plane when the actuating member in the treatment portion is in an open state.

In the actuating members 20A and 20B, the intermediate link 15 and the manipulation block 17 configured in this manner, by moving (pulling back) the open-close manipulation wire 18 closer to the proximal end side than the longitudinal axis member 41, the actuating members 20A and 20B rotate around the fixing pin 12 such that a distal end side of the first actuating member 20A and a distal end side of the second actuating member 20B become relatively closer to each other, for example, the actuating members 20A and 20B come in contact with each other. Accordingly, the distal end side of the first actuating member 20A and the distal end side of the second actuating member 20B are in a closed state in which they cannot be any closer to each other. On the other hand, when the open-close manipulation wire 18 is moved (pushed) to the distal side relative to the longitudinal axis member 41, as shown in FIG. 6, the distal end side of the first actuating member 20A and the distal end side of the second actuating member 20B are separated, for example, the manipulation block 17 comes in contact with the actuating members 20A and 20B, and therefore the distal end side of the first actuating member 20A and the distal end side of the second actuating member 20B are in an open state in which they cannot be separated any further.

In this manner, the actuating members 20A and 20B can perform an open-close operation which open and close along a second axis Y perpendicular to (intersecting) the first axis X by advancing and retracting the open-close manipulation wire 18 along the first axis X.

Here, a third axis Z perpendicular to both the first axis X and the second axis Y is defined. In this example, each of the actuating members 20A and 20B is formed to be symmetrical with respect to a reference plane T1 perpendicular to the third axis Z shown in FIG. 2. The actuating members 20A and 20B rotate on the reference plane T1.

As shown in FIG. 2 and FIG. 5, the through-holes 25A, 26A, 27A, and 28A penetrating through the wall portion 21A are formed in the wall portion 21A of the first actuating member 20A. In this example, the through-holes 25A and 26A extend along the first axis X, and the through-holes (a first restricting portion and a first through-hole) 27A and 28A extend along the third axis Z. The through-holes 25A and 26A are formed to be symmetrical with respect to the reference plane T1 on the distal end surface 23A of the wall portion 21A. The through-holes 28A and 27A are formed to be symmetrical with respect to the reference plane T1 at more proximal side than the through-holes 25A and 26A. The through-holes 26A and 27A are formed in a first orientation Z1 (one side) along the third axis Z than the reference plane T1, and the through-holes 25A and 28A are formed in a second orientation Z2 (the other side) along the third axis Z than the reference plane T1. The through-holes 25A, 26A, 27A, and 28A are formed on a reference plane T2 (refer to FIG. 5) perpendicular to the second axis Y.

That is, the through-hole 27A is formed at more proximal side and at the first orientation Z1 along the third axis Z side in comparison with the through-hole 25A. The through-hole 28A is formed at more proximal side and at the second orientation Z2 along the third axis Z side in comparison with the through-hole 26A. In a direction along the third axis Z, the through-hole 26A is formed between the through-hole 25A and the through-hole 27A, and the through-hole 25A is formed between the through-hole 26A and the through-hole 28A.

Figure 7:
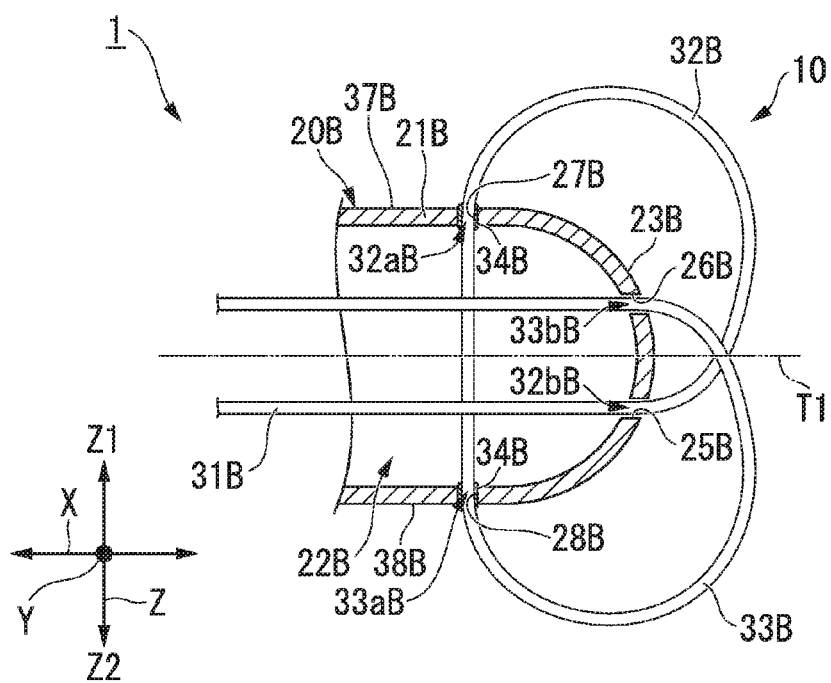
FIG. 7 is a cross-sectional view along an X-Z plane of a second actuating member of the treatment portion.

Similarly, as shown in FIG. 7, a through-hole (a second restricting portion and a second through-hole) 27B is formed at more proximal side and at the first orientation Z1 along the third axis Z side in comparison with a through-hole 25B. A through-hole 28B is formed at more proximal side and at the second orientation Z2 along the third axis Z side in comparison with a through-hole 26B. In a direction along the third axis Z, the through-hole 26B is formed between the through-hole 25B and the through-hole 27B, and the through-hole 25B is formed between the through-hole 26B and the through-hole 28B.

A first wire (a wire member) 31A is formed of a material having elasticity and flexibility such as stainless steel. A super-elastic wire using, for example, a NiTi alloy, may be used as the first wire 31A, and the first wire 31A may have a pre-shape.

The first wire 31A that has passed through the internal space 22A forms the first loop portion 32A which is curved in a loop shape between a point existing to the outside of the first actuating member 20A through the through-hole 25A and a point returning to the internal space 22A through the through-hole 27A. The through-hole 27A restricts an extending direction of a first end portion (one end portion) 32aA of the first loop portion 32A in a direction along the third axis Z which intersects an outer side surface 37A of the first actuating member 20A. The first loop portion 32A is likely to become longer along the third axis Z by passing the first loop portion 32A through the through-hole 27A.

The first end portion 32aA of the first loop portion 32A is curved in a loop shape such that the first end portion 32aA of the first loop portion 32A intersects the outer side surface 37A of the first actuating member 20A and extends to the outside of the outer side surface 37A of the first actuating member 20A. The first end portion 32aA of the first loop portion 32A is fixed to the first actuating member 20A with a fixing member 34A such as a brazing or soldering material at the through-hole 27A. In other words, the through-hole 27A holds the first end portion 32aA of the first loop portion 32A.

The second end portion (the other end portion) 32bA of the first loop portion 32A inserted into the through-hole 25A is held at a distal end portion of the first actuating member 20A. The first end portion 32aA of the first loop portion 32A is disposed at more proximal side than the second end portion 32bA of the first loop portion 32A.

The first wire 31A exits again to the outside of the first actuating member 20A through the through-hole 28A. The first wire 31A positioned outside from the through-hole 28A forms the third loop portion 33A which is curved in a loop shape until it returns to the internal space 22A through the through-hole 26A. The through-hole 28A restricts an extending direction of a first end portion (one end portion) 33aA of the third loop portion 33A in a direction along the third axis Z which intersects an outer side surface 38A of the first actuating member 20A.

The first end portion 33aA of the third loop portion 33A intersects the outer side surface 38A of the first actuating member 20A, extends to the outside of the outer side surface 38A of the first actuating member 20A and is curved in a loop shape. The through-hole 28A fixes the first end portion 33aA of the third loop portion 33A to the first actuating member 20A by the fixing member 34A. A second end portion (the other end portion) 33bA of the third loop portion 33A inserted into the through-hole 26A is held at the distal end portion of the first actuating member 20A. The first end portion 33aA of the third loop portion 33A is disposed at more proximal side than the second end portion 33bA of the third loop portion 33A.

In this manner, the loop portions 32A and 33A are formed to protrude from the first actuating member 20A. The second end portion 32bA of the first loop portion 32A intersects the second end portion 33bA of the third loop portion 33A. The first loop portion 32A and the third loop portion 33A are disposed to shift with each other along the third axis Z.

In FIG. 5, shapes of the first loop portion 32A and the third loop portion 33A are set as loop shapes B1 and B2, respectively. An area surrounded by the first actuating member 20A and one of the first loop portion 32A and the third loop portion 33A is defined as a grasping area R1.

A second wire (a wire member) 31B shown in FIG. 7 is configured similarly to the first wire 31A. The second wire 31B that has passed through an internal space 22B forms the second loop portion 32B which is curved in a loop shape between a point existing to the outside of the second actuating member 20B through the through-hole 25B and a point returning to the internal space 22B through the through-hole 27B. The through-hole 27B restricts an extending direction of a first end portion (one end portion) 32aB of the second loop portion 32B in a direction along the third axis Z which intersects an outer side surface 37B of the second actuating member 20B. The first end portion 32aB of the second loop portion 32B intersects the outer side surface 37B of the second actuating member 20B, extends to the outside of the outer side surface 37B of the second actuating member 20B and is curved in a loop shape. The through-hole 27B fixes the first end portion 32aB of the second loop portion 32B to the second actuating member 20B via a fixing member 34B. In other words, the through-hole 27B holds the first end portion 32aB of the second loop portion 32B. A second end portion (the other end portion) 32bB of the second loop portion 32B inserted into the through-hole 25B is held at a distal end portion of the second actuating member 20B. The first end portion 32aB of the second loop portion 32B is disposed at more proximal side than the second end portion 32bB of the second loop portion 32B.

The second wire 31B exits again to the outside of the second actuating member 20B through the through-hole 28B. The second wire 31B that has exited to the outside from the through-hole 28B forms the fourth loop portion 33B that is curved in a loop shape ending when it returns to the internal space 22B through the through-hole 26B. The through-hole 28B restricts an extending direction of a first end portion (one end portion) 33aB of the fourth loop portion 33B in a direction along the third axis Z which intersects an outer side surface 38B of the second actuating member 20B. In this manner, the loop portions 32B and 33B are formed to protrude from the second actuating member 20B. The second end portion 32bB of the second loop portion 32B intersects a second end portion (the other end portion) 33bB of the fourth loop portion 33B. The second loop portion 32B and the fourth loop portion 33B are positioned that are shifted along the third axis Z.

A pair of end portions of the first wire 31A are connected to a distal end portion of an advancing and retracting manipulation wire 36A shown in FIG. 3, for example, inside the longitudinal axis member 41, by brazing or the like. A pair of end portions of the second wire 31B are also connected to a distal end portion of an advancing and retracting manipulation wire 36B. The advancing and retracting manipulation wire 36A is inserted into the lumen 41b of the longitudinal axis member 41 in an advanceable and retractable manner. The advancing and retracting manipulation wire 36B is inserted into the lumen 41c of the longitudinal axis member 41 in an advanceable and retractable manner. The open-close manipulation wire 18 is inserted into the lumen 41a of the longitudinal axis member 41 in an advanceable and retractable manner.

Figure 8:
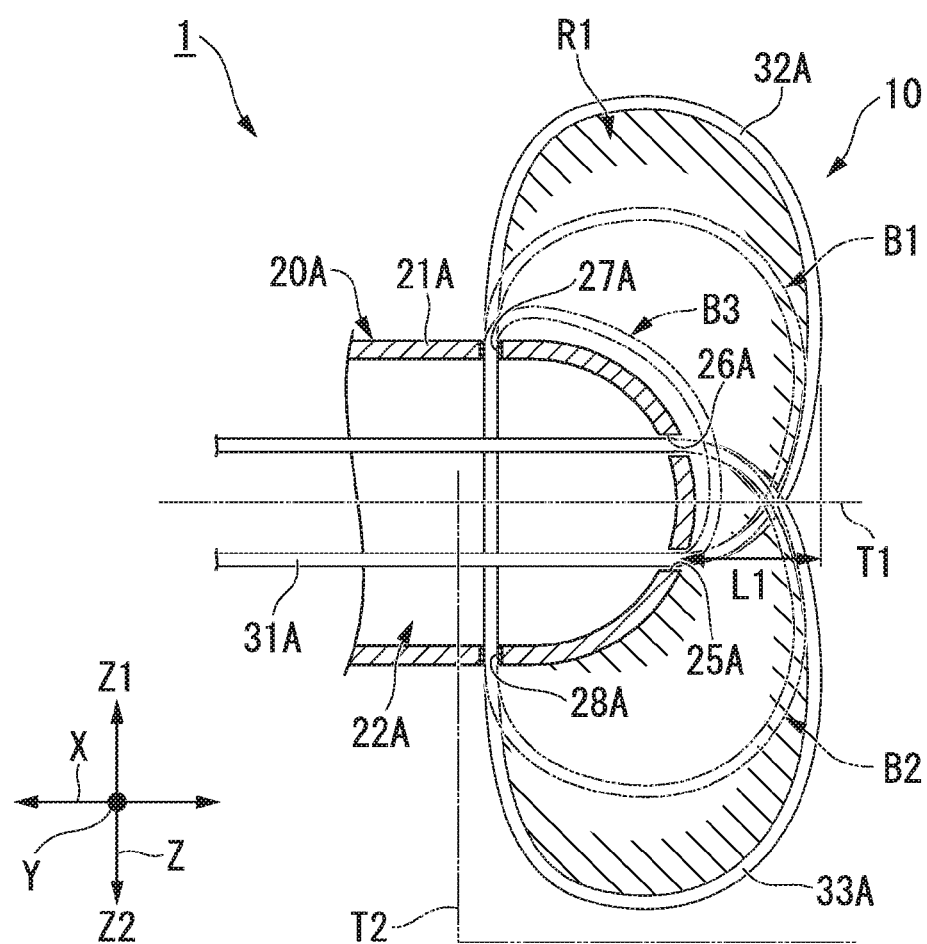
FIG. 8 is a cross-sectional view along the X-Z plane which describes a state in which both loop portions of the first actuating member goes to protrude.

When the advancing and retracting manipulation wire 36A is pushed, the first wire 31A further protrudes from the through-holes 25A and 26A as shown in FIG. 8. Since the first wire 31A is fixed at a position of the through-hole 27A, the first loop portion 32A further protrudes mainly in the first orientation Z1 along the third axis Z with respect to the above-described loop shape B1 (an outer diameter of the first loop portion 32A increases). In other words, the first loop portion 32A has an oblong shape. When the first loop portion 32A protrudes in this manner, even if the advancing and retracting manipulation wire 36A is pushed, a distance L1 between the through-hole 25A formed on the distal end surface 23A of the first actuating member 20A and a distal end of the first loop portion 32A along the first axis X is less likely to become longer.

Similarly to the first loop portion 32A, when the advancing and retracting manipulation wire 36A is pushed, the third loop portion 33A protrudes mainly in the second orientation Z2 along the third axis Z. In this manner, the grasping area R1 becomes longer mainly along the third axis Z, and a size of the grasping area R1 becomes wider.

On the other hand, when the advancing and retracting manipulation wire 36A is pulled back, the first loop portion 32A is retracted as shown in a loop shape B3. The phrase "first loop portion 32A is retracted" herein does not mean that the first loop portion 32A is completely accommodated inside the first actuating member 20A but that a protrusion length of the first loop portion 32A that protrudes from the first actuating member 20A become shortens. When a groove or the like is provided on an outer surface of the first actuating member 20A and the loop portions 32A and 33A are accommodated inside the groove, the loop portions 32A and 33A may be completely retracted inside the first actuating member 20A by providing a groove or the like on an outer surface of the first actuating member 20A and accommodating the loop portions 32A and 33A inside the groove.

In this manner, the first loop portion 32A and the third loop portion 33A can protrude from the first actuating member 20A and can be retracted to the first actuating member 20A side by manipulating the advancing and retracting manipulation wire 36A. Similarly, the second loop portion 32B and the fourth loop portion 33B can protrude from the second actuating member 20B and can be retracted to the second actuating member 20B side by manipulating the advancing and retracting manipulation wire 36B.

As shown in FIG. 3, the manipulation portion 50 of the tissue grasping device 1 includes a manipulation portion main body 51, and an opening and closing manipulation member 56 and advancing and retracting manipulation members 57 and 58 which are slidably provided with respect to the manipulation portion main body 51. A proximal end portion of the longitudinal axis member 41 is coupled to the manipulation portion main body 51. A proximal end portion of the open-close manipulation wire 18 is coupled to the opening and closing manipulation member 56. Proximal end portions of the advancing and retracting manipulation wires 36A and 36B are coupled to the advancing and retracting manipulation members 57 and 58, respectively. Accordingly, when an operator performs a slide manipulation on the opening and closing manipulation member 56, the open-close manipulation wire 18 is moved along the first axis X relative to the longitudinal axis member 41 so that the actuating members 20A and 20B can perform an opening and closing operation. In addition, when the operator performs a slide manipulation on the advancing and retracting manipulation member 57, the loop portions 32A and 33A can protrude or can be retracted through the advancing and retracting manipulation wire 36A at one time. The loop portions 32A and 33A project from and are retracted into the reference plane T2. The loop portions 32B and 33B can protrude or can be retracted through the advancing and retracting manipulation wire 36B at one time by sliding the advancing and retracting manipulation member 58.

Figure 9:
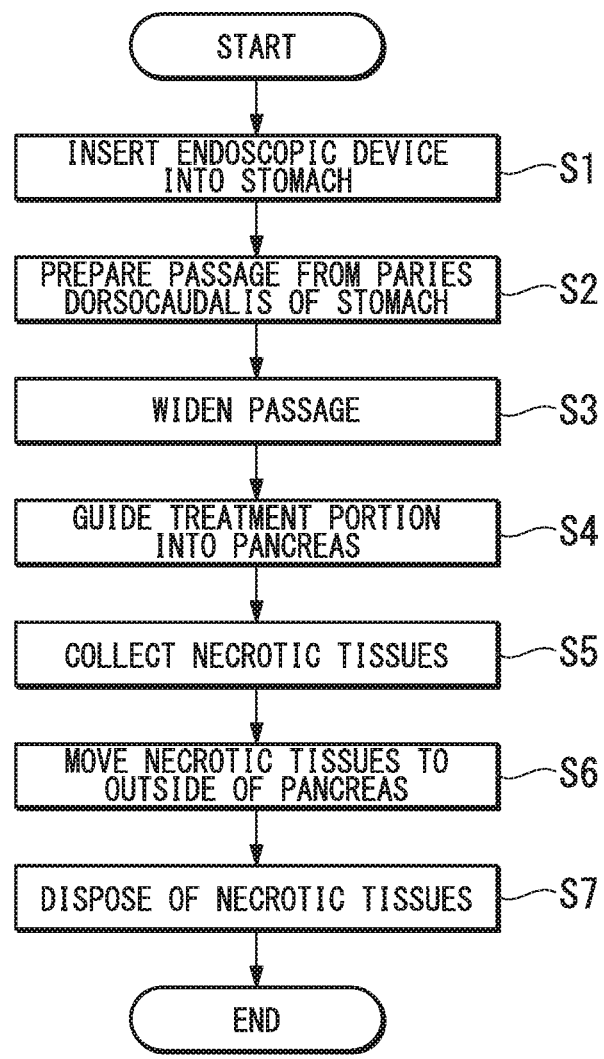
FIG. 9 is a flowchart showing an operation of pancreatic necrosectomy using the tissue grasping device.

Next, operations of the tissue grasping device 1 configured as described above will be described by exemplifying an operation of pancreatic necrosectomy using the tissue grasping device 1. FIG. 9 is a flowchart showing an operation of pancreatic necrosectomy using the tissue grasping device 1. In order to perform this operation, the endoscopic device 300, the endoscopic high frequency knife 310 (refer to FIG. 11), a dilatation catheter for an endoscope 320 (refer to FIG. 12), and the tissue grasping device 1 of the present embodiment are used.

Before the operation starts, in the tissue grasping device 1 of the present embodiment, the actuating members 20A and 20B are in a closed state by pulling back the open-close manipulation wire 18 via the opening and closing manipulation member 56. By pulling back the advancing and retracting manipulation wires 36A and 36B via the advancing and retracting manipulation members 57 and 58, the loop portions 32A, 33A, 32B, and 33B are in a reduced state in which outer diameters are reduced to a minimum size, for example, in the above-described loop shape B3.

Figure 10:
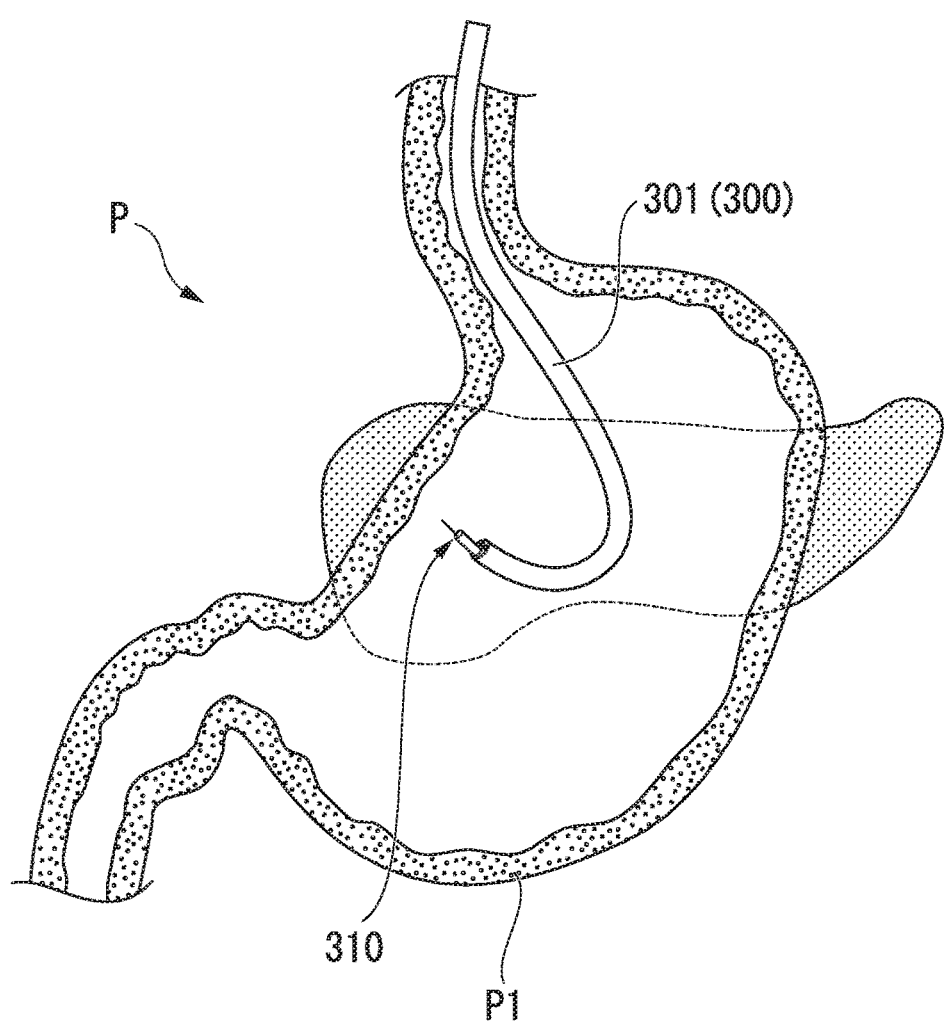
FIG. 10 is a diagram showing pancreatic necrosectomy using the tissue grasping device.
Figure 11:
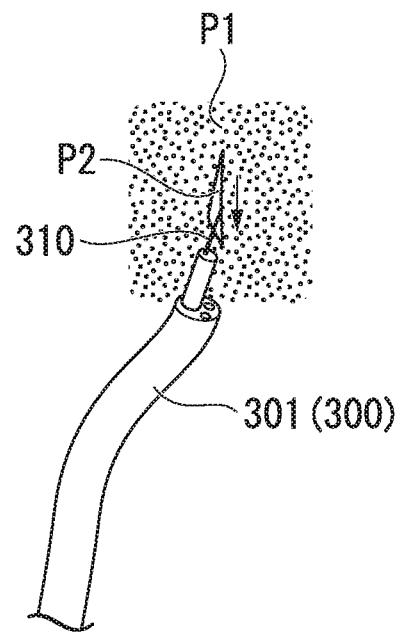
FIG. 11 is a diagram showing pancreatic necrosectomy using the tissue grasping device.

First, the endoscope insertion portion 301 of the endoscopic device 300 is inserted into the stomach of a patient (Step S1 shown in FIG. 9). In Step S1, as shown in FIG. 10, the endoscope insertion portion 301 of the endoscopic device 300 is positioned inside a stomach P1 through the esophagus from the mouth (not shown) of a patient P. In this operation, the operator selects an appropriate region to be incised by observing the inside of the stomach P1 using an endoscopic image. Here, Step S1 is terminated, and the operation proceeds to Step S2.

Step S2 is a step in which a panes dorsocaudalis of the stomach P1 is incised, and a passage for guiding the tissue grasping device 1 into the pancreas is formed in the stomach P1 and the pancreas. In Step S2, the above-described endoscopic high frequency knife 310 is attached to the treatment tool channel 302 of the endoscopic device 300 in order to incise the region selected in Step S1. The operator makes a hole in the panes dorsocaudalis of the stomach P1 using the endoscopic high frequency knife 310 and makes a passage (an opening portion) P2 (refer to FIG. 11). Here, Step S2 is terminated and the operation proceeds to Step S3.

Step S3 is a step in which the passage P2 formed in Step S2 is widened. In Step S3, a guide wire (not shown) is introduced into the body through an inner tube (not shown) provided in the endoscopic high frequency knife 310. Further, the dilatation catheter for an endoscope 320 is introduced into the body along the guide wire. A distal end of the dilatation catheter for an endoscope 320 is guided into the passage P2 formed in the stomach P1 by the guide wire. When the dilatation catheter for an endoscope 320 is guided into the passage P2, a balloon portion of the dilatation catheter for an endoscope 320 is inserted into the passage P2 formed in Step S2.

Figure 12:
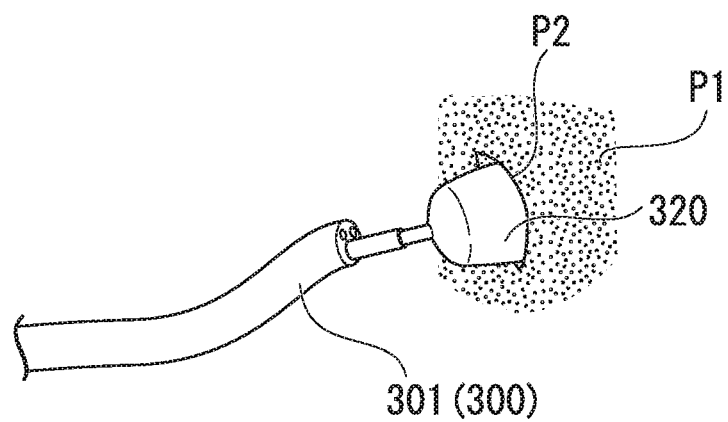
FIG. 12 is a diagram showing pancreatic necrosectomy using the tissue grasping device.
Figure 13:
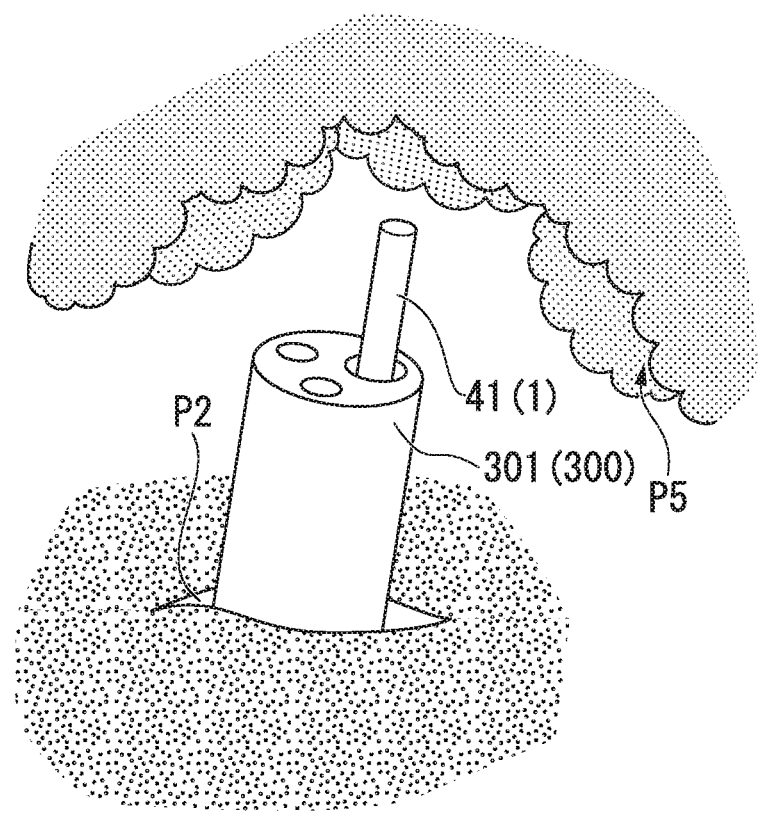
FIG. 13 is a diagram showing pancreatic necrosectomy using the tissue grasping device.
Figure 14:
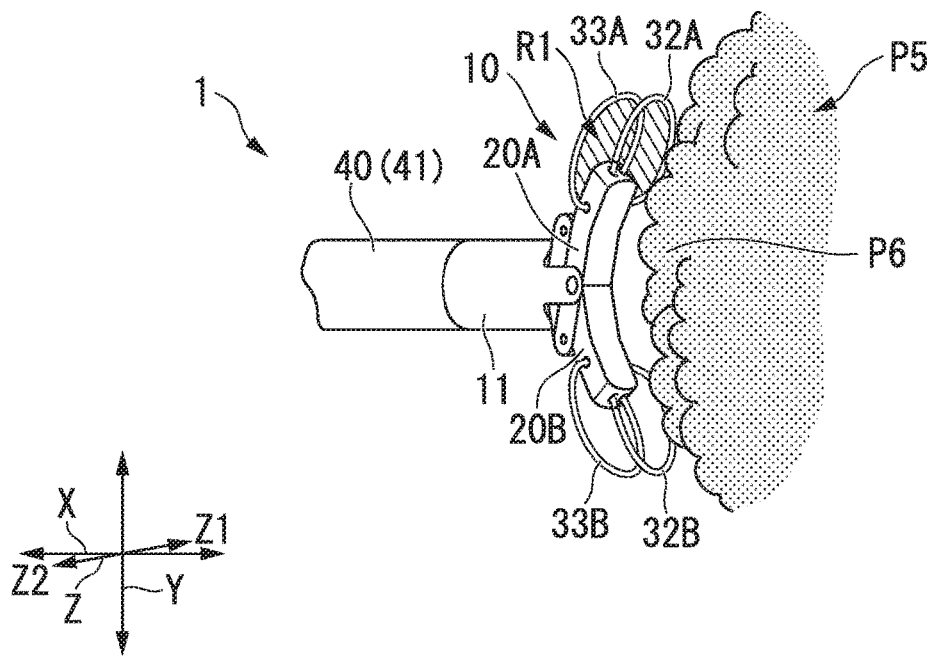
FIG. 14 is a diagram showing pancreatic necrosectomy using the tissue grasping device.

Then, the balloon portion is inflated and the passage P2 is pushed and widened to a desired size, as shown in FIG. 12. Accordingly, in Step S3, the passage P2 that has been widened to a size at which the treatment portion 10 can be inserted into the pancreas from the inside of the stomach P1 is formed in the stomach P1 and the pancreas. In order to further widen the passage P2, for example, a high frequency treatment tool configured to incise biological tissues using a high frequency current is used. When the passage P2 of the desired size is formed, the dilatation catheter for an endoscope 320 is removed. Here, Step S3 is terminated and the operation proceeds to Step S4.

Step S4 is a step in which the treatment portion 10 is guided into the pancreas through the passage P2 that is widened in Step S3. In Step S4, the tissue grasping device 1 is attached to the treatment tool channel 302 of the endoscopic device 300 (refer to FIG. 1). In addition, the endoscopic high frequency knife 310 and the dilatation catheter for an endoscope 320 are removed from the treatment tool channel 302, and the tissue grasping device 1 may be attached to the empty treatment tool channel 302. The treatment portion 10 and the insertion portion 40 of the tissue grasping device 1 are inserted into the treatment tool channel 302. The distal end of the longitudinal axis member 41 of the tissue grasping device 1 protrudes from a distal end of the treatment tool channel 302. Since the loop portions 32A, 33A, 32B, and 33B are in a reduced state, the treatment portion 10 of the tissue grasping device 1 is likely to be inserted into the treatment tool channel 302. Then, the operator who manipulates the endoscopic device 300 to which the tissue grasping device 1 is attached bends and moves the endoscope insertion portion 301 of the endoscopic device 300, and therefore guides a distal end portion of the longitudinal axis member 41 into the pancreas P5 through the passage P2 formed in the stomach P1 and the pancreas P5 (refer to FIG. 13). When the tissue grasping device 1 enters the pancreas P5, the guide wire is removed. Here, Step S4 is terminated and the operation proceeds to Step S5.

Step S5 is a step in which the treatment portion 10 guided into the pancreas P5 in Step S4 is used to collect necrotic tissues. In Step S5, the operator adjusts a position of the treatment portion 10 by using an image observed through the endoscopic device 300. Next, the operator moves a distal end of the endoscope insertion portion 301 of the endoscopic device 300 while targeting necrotic tissues to be collected inside the pancreas P5. When front distal ends of the actuating members 20A and 20B reach positions that face necrotic tissues P6 of the pancreas P5 shown in FIG. 14, the advancing and retracting manipulation members 57 and 58 are pushed. The loop portions 32A and 32B protrude in the first orientation Z1 along the third axis Z. The loop portions 33A and 33B protrude in the second orientation Z2 along the third axis Z. Accordingly, the grasping area R1 of the treatment portion 10 becomes longer along the third axis Z. When the advancing and retracting manipulation members 57 and 58 are pushed, it is preferable that the loop portions 32A and 33A and the loop portions 32B and 33B have substantially the same size. Next, the opening and closing manipulation member 56 is pushed. Accordingly, the actuating members 20A and 20B are in an open state.

Figure 15:
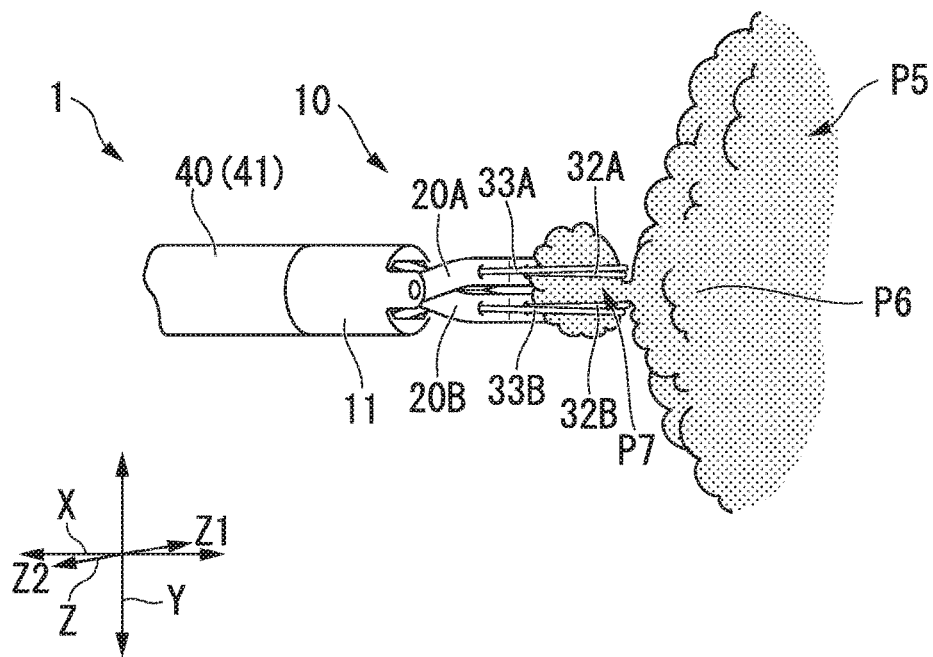
FIG. 15 is a diagram showing pancreatic necrosectomy using the tissue grasping device.

Next, while the operator presses the loop portions 32A, 33A, 32B, and 33B against the necrotic tissues P6, the actuating members 20A and 20B are in a closed state, as shown in FIG. 15. A distance L1 between distal ends of the loop portions 32A, 33A, 32B, and 33B and the throughholes 25A and 25B is less likely to become longer by protruding the loop portions 32A, 33A, 32B, and 33B along the third axis Z. Therefore, a force sufficient to grasp the necrotic tissues P6 is applied to the loop portions 32A, 33A, 32B, and 33B by pulling back the opening and closing manipulation member 56. The second end portion 32bA of the first loop portion 32A intersects the second end portion 33bA of the third loop portion 33A. The second end portion 32bB of the second loop portion 32B intersects the second end portion 33bB of the fourth loop portion 33B. Accordingly, the necrotic tissues P6 grasped by the loop portions 32A, 33A, 32B, and 33B are less likely to fall out along the second axis Y.

When the necrotic tissues P6 are grasped by the loop portions 32A, 33A, 32B, and 33B, distal end portions of the loop portions 32A, 33A, 32B, and 33B are used in many cases. In addition, surfaces of the necrotic tissues P6 are sticky. Accordingly, when the loop portions 32A, 33A, 32B, and 33B protrude along the third axis Z and become longer along the third axis Z, a great amount of the necrotic tissues P6 can stick to the loop portions 32A, 33A, 32B, and 33B and efficiently grasped.

Figure 16:
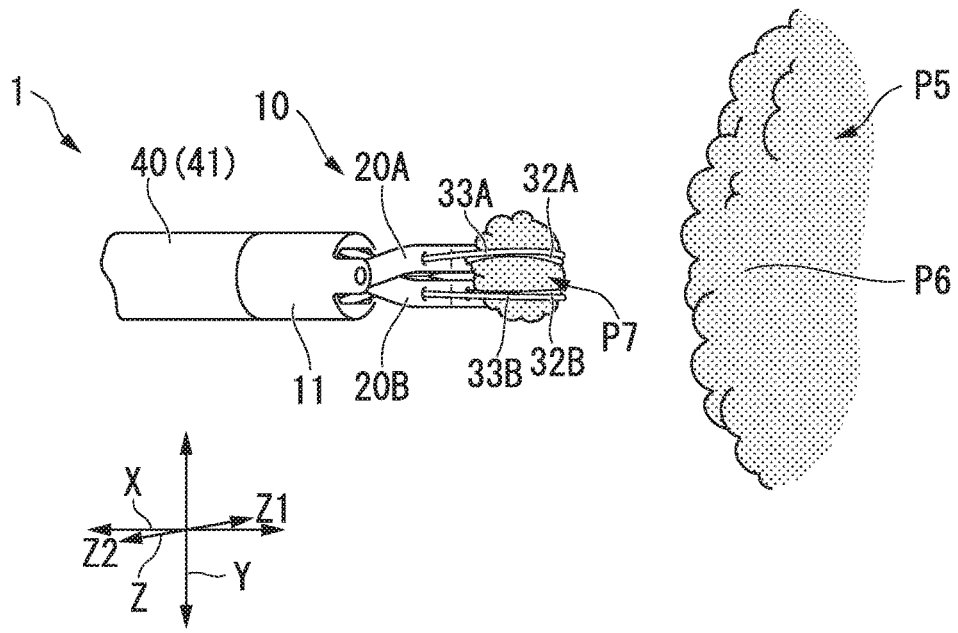
FIG. 16 is a diagram showing pancreatic necrosectomy using the tissue grasping device.

Grasping tissues P7 are dissected from the necrotic tissues P6 by pulling back the manipulation portion 50 while the actuating members 20A and 20B are in a closed state as shown in FIG. 16. Since the grasping area R1 becomes longer along the third axis Z, it is possible to dissect a great amount of the grasping tissues P7 at one time. Without incision for disconnecting the grasping tissues P7 from the necrotic tissues P6, the grasping tissues P7 are dissected from the necrotic tissues P6 by pulling back the manipulation portion 50 while the grasping tissues P7 are grasped by the loop portions 32A, 33A, 32B, and 33B. The dissected grasping tissues P7 are collected by the tissue grasping device 1 while the loop portions 32A, 33A, 32B, and 33B are interposed therebetween.

The wires 31A and 31B of the loop portions 32A, 33A, 32B, and 33B included in the tissue grasping device 1 of the present embodiment are formed in a loop shape. Accordingly, since a great amount of the necrotic tissues P6 is interposed between the loop portions 32A, 33A, 32B, and 33B that became longer along the third axis Z, it is possible to capture some of the necrotic tissues P6 in a loop of the wires 31A and 31B according to an interposing force. In addition, when the grasping tissues P7 are collected, the advancing and retracting manipulation wires 36A and 36B are pulled back. Accordingly, outer diameters of the loop portions 32A, 33A, 32B, and 33B are reduced, and the grasping tissues P7 are reliably maintained by the loop portions 32A, 33A, 32B, and 33B. Also, the outer diameters of the loop portions 32A, 33A, 32B, and 33B can be adjusted in advance according to a size of the grasping tissues P7 to be removed. Therefore, it is possible to easily set an appropriate loop diameter at which an amount of ungrasped tissues among the grasping tissues P7 is small. Here, Step S5 is terminated and the operation proceeds to Step S6.

Step S6 is a step in which the necrotic tissues P6 (the grasping tissues P7) collected in Step S5 are moved to the outside of the pancreas P5. The operator sets the actuating members 20A and 20B in a closed state, moves the endoscope insertion portion 301 of the endoscopic device 300, moves the longitudinal axis member 41 of the tissue grasping device 1 to the treatment tool channel 302, and therefore pulls back the treatment portion 10 from the inside of the pancreas P5 into the stomach P1. Therefore, Step S6 ends and the operation proceeds to Step S7.

Step S7 is a step in which the necrotic tissues P6 are disposed of in the stomach P1. In Step S7, first, the operator sets the actuating members 20A and 20B in an open state. In addition, the outer diameters of the loop portions 32A, 33A, 32B, and 33B increase. In this manner, the grasping tissues P7 grasped by the loop portions 32A, 33A, 32B, and 33B are disposed in the stomach P1. At this time, when the grasping tissues P7 are entangled and adhered to the wires 31A and 31B so that they are not easily moved, the operator retracts the loop portions 32A, 33A, 32B, and 33B to the actuating members 20A and 20B. Accordingly, the removal of the grasping tissues P7 is promoted.

The grasping tissues P7 disposed in the stomach P1 are excreted through the gastrointestinal tract. In addition, in Step S7, the treatment portion 10 in which the grasping tissues P7 are accommodated may be removed to the outside of the body as necessary. In this case, the entire tissue grasping device 1 may be removed to the outside of the body with the endoscopic device 300. when the treatment portion 10 maintaining the grasping tissues P7 has a size at which it can be retracted into the treatment tool channel 302, the treatment portion 10 in which the grasping tissues P7 are accommodated may be removed to the outside of the body through the treatment tool channel 302. The grasping tissues P7 removed to the outside of the body can be used for a pathological examination and the like. Here, Step S7 is terminated.

In this operation, when an amount of the necrotic tissues P6 that need to be removed from the inside of the pancreas P5 is very large, steps of Step S4 to Step S7 can be repeated a plurality of times.

Here, a shape of the loop portion is examined. When a pair of through-holes are formed on the distal end surface of the actuating member and a wire protrudes from the pair of through-holes to form a loop portion, the loop portion becomes longer in a longitudinal direction of the tissue grasping device. In other words, the loop portion has a vertically long shape in the first axis X. Therefore, a distance between the distal end surface of the actuating member and the distal end of the loop portion is likely to become longer. In addition, when the loop portion has the vertically long shape in the first axis X, a size of the grasping area, which is an area surrounded by the loop portion and the actuating member, is less likely to increase.

On the other hand, according to the tissue grasping device 1 of the present embodiment, when the first wire 31A further protrudes from the through-hole 25A, the first loop portion 32A configured by the first wire 31A further protrudes in the first orientation Z1 along the third axis Z. Similarly, the second loop portion 32B protrudes in the first orientation Z1 along the third axis Z, and the third loop portion 33A and the fourth loop portion 33B further protrudes in the second orientation Z2 along the third axis Z. In this manner, when the loop portions 32A, 33A, 32B, and 33B set to become longer along the third axis Z and the necrotic tissues P6 are grasped by the loop portions 32A, 33A, 32B, and 33B, it is possible to collect a great amount of necrotic tissues at one time.

When the loop portions 32A, 33A, 32B, and 33B further protrude from the actuating members 20A and 20B, the loop portions 32A, 33A, 32B, and 33B become longer along the third axis Z. A distance L1 between the distal end surfaces 23A and 23B of the actuating members 20A and 20B and the distal ends of the loop portions 32A, 33A, 32B, and 33B is less likely to become longer. Accordingly, a force sufficient to grasp the necrotic tissues P6 can be applied to the loop portions 32A, 33A, 32B, and 33B by pulling back the opening and closing manipulation member 56. In addition, since the loop portions 32A, 33A, 32B, and 33B have an oblong shape when the loop portions 32A, 33A, 32B, and 33B protrude, a size of the grasping area R1 becomes wider, and a greater amount of the necrotic tissues P6 can be grasped.

The first loop portion 32A intersects the third loop portion 33A. The second loop portion 32B intersects the fourth loop portion 33B. Therefore, it is possible to prevent the necrotic tissues P6 grasped by the loop portions 32A, 33A, 32B, and 33B from falling out along the second axis Y.

The loop portions 32A and 33A can project from and can be retracted to the first actuating member 20A. The loop portions 32B and 33B can project from and can be retracted to the second actuating member 20B. Accordingly, the loop portions 32A, 33A, 32B, and 33B are in a reduced state when the tissue grasping device 1 is inserted into the treatment tool channel 302 of the endoscopic device 300, and therefore the tissue grasping device 1 can be easily inserted into the treatment tool channel 302.

Figure 17:
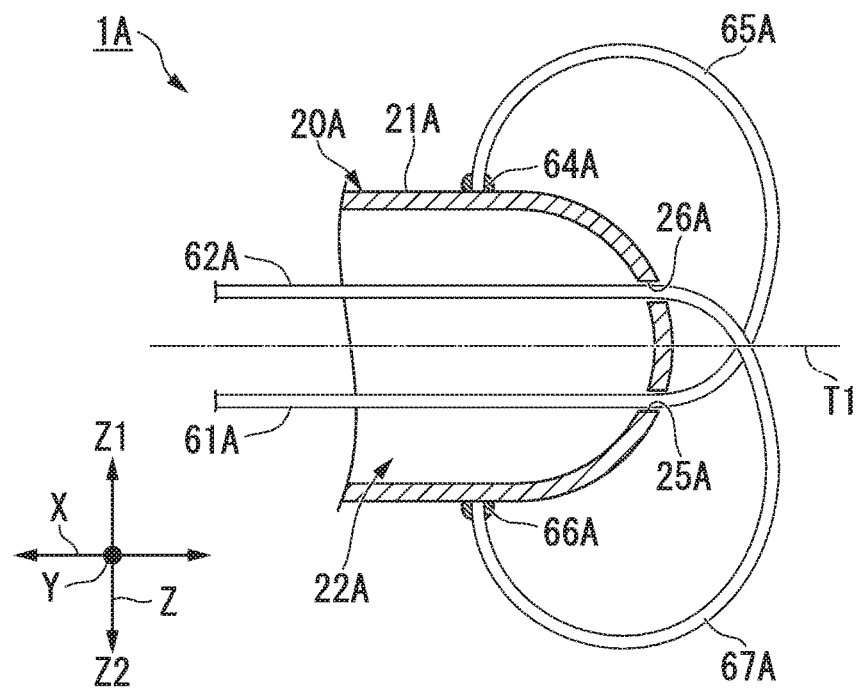
FIG. 17 is a cross-sectional view along the X-Z plane of a first actuating member in a modified example of the tissue grasping device of the first embodiment of the present invention.

In the present embodiment, like a tissue grasping device 1A shown in FIG. 17, a first wire (a wire member) 61A and a third wire (a wire member) 62A may not be integrally formed but may be separately formed. In this modified example, the through-holes 27A and 28A are not formed in the first actuating member 20A.

The first wire 61A that has passed through the internal space 22A forms a first loop portion 65A between a point existing to the outside of the first actuating member 20A through the through-hole 25A and a point being fixed to the wall portion 21A by a fixing member (a first restricting portion) 64A. On the other hand, the third wire 62A that has passed through the internal space 22A forms a third loop portion 67A between a point existing to the outside of the first actuating member 20A through the through-hole 26A and a point being fixed to the wall portion 21A by a fixing member 66A. An end portion at a side opposite to an end portion fixed by the fixing member 64A of the first wire 61A and an end portion at a side opposite to an end portion fixed by the fixing member 66A of the third wire 62A are connected to the distal end portion of the advancing and retracting manipulation wire 36A.

In the tissue grasping device 1A of the modified example configured in this manner, when the advancing and retracting manipulation wire 36A is pushed, the first wire 61A further protrudes from the through-hole 25A, and the first loop portion 65A further protrudes in the first orientation Z1 along the third axis Z. The third wire 62A further protrudes from the through-hole 26A. The third loop portion 67A further protrudes in the second orientation Z2 along the third axis Z.

Figure 18:
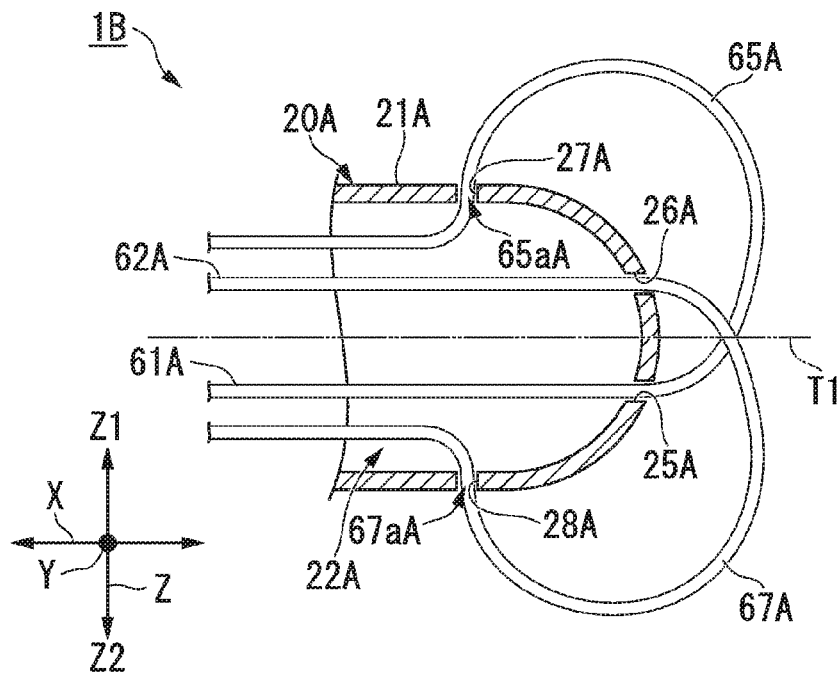
FIG. 18 is a cross-sectional view along the X-Z plane of the first actuating member in the modified example of the tissue grasping device of the first embodiment of the present invention.

In the tissue grasping device 1A of the modified example, a configuration in which the wires 61A and 62A are not fixed may be provided, like a tissue grasping device 1B shown in FIG. 18. Specifically, the first wire 61A that has passed through the internal space 22A forms the first loop portion 65A between a point existing to the outside of the first actuating member 20A through the through-hole 25A and a point returning to the internal space 22A through the through-hole 27A. A first end portion 65aA of the first loop portion 65A is inserted into the through-hole 27A. The third wire 62A that has passed through the internal space 22A forms the third loop portion 67A between a point existing to the outside of the first actuating member 20A through the through-hole 26A and a point returning to the internal space 22A through the through-hole 28A. A first end portion 67aA of the third loop portion 67A is inserted into the through-hole 28A. Both end portions of the first wire 61A and both end portions of the third wire 62A are connected to the distal end portion of the advancing and retracting manipulation wire 36A.

In the tissue grasping device 1B of the modified example configured in this manner, when the advancing and retracting manipulation wire 36A is pushed, the first wire 61A further protrudes from both of the through-holes 25A and 27A and the third wire 62A further protrudes from both of the through-holes 26A and 28A.

Second Embodiment

Next, a second embodiment of the present invention will be described with reference to FIG. 19 to FIG. 21. The same components as in the above embodiment are denoted with the same reference numerals, descriptions thereof will be omitted, and only different points will be described.

Figure 19:
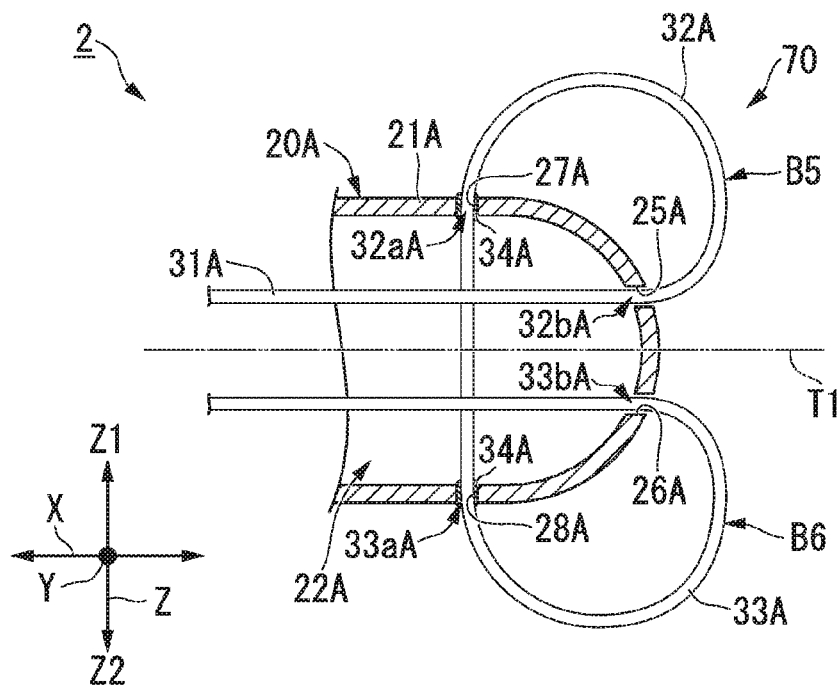
FIG. 19 is a cross-sectional view along the X-Z plane of a first actuating member in a tissue grasping device of a second embodiment of the present invention.

As shown in FIG. 19, a tissue grasping device 2 of the present embodiment includes a treatment portion 70 in place of the treatment portion 10 of the first embodiment. In the treatment portion 70, the through-holes 25A and 26A formed in the first actuating member 20A are disposed differently from those of the treatment portion 10.

The through-hole 25A is disposed in the first orientation Z1 along the third axis Z side in comparison with the through-hole 26A. That is, based on the reference plane T1, the through-holes 25A and 27A are formed in the first orientation Z1 along the third axis Z, and the through-holes 26A and 28A are formed in the second orientation Z2 along the third axis Z. The second end portion 32bA of the first loop portion 32A and the second end portion 33bA of the third loop portion 33A are substantially parallel (or may be parallel). In other words, the first loop portion 32A and the third loop portion 33A do not intersect. The first wire 31A is fixed to the wall portion 21A at the through-hole 27A and the through-hole 28A by the above-described fixing member 34A. A pair of end portions of the first wire 31A are connected to the distal end portion of the advancing and retracting manipulation wire 36A. In FIG. 19, shapes of the first loop portion 32A and the third loop portion 33A are set as loop shapes B5 and B6.

Figure 20:
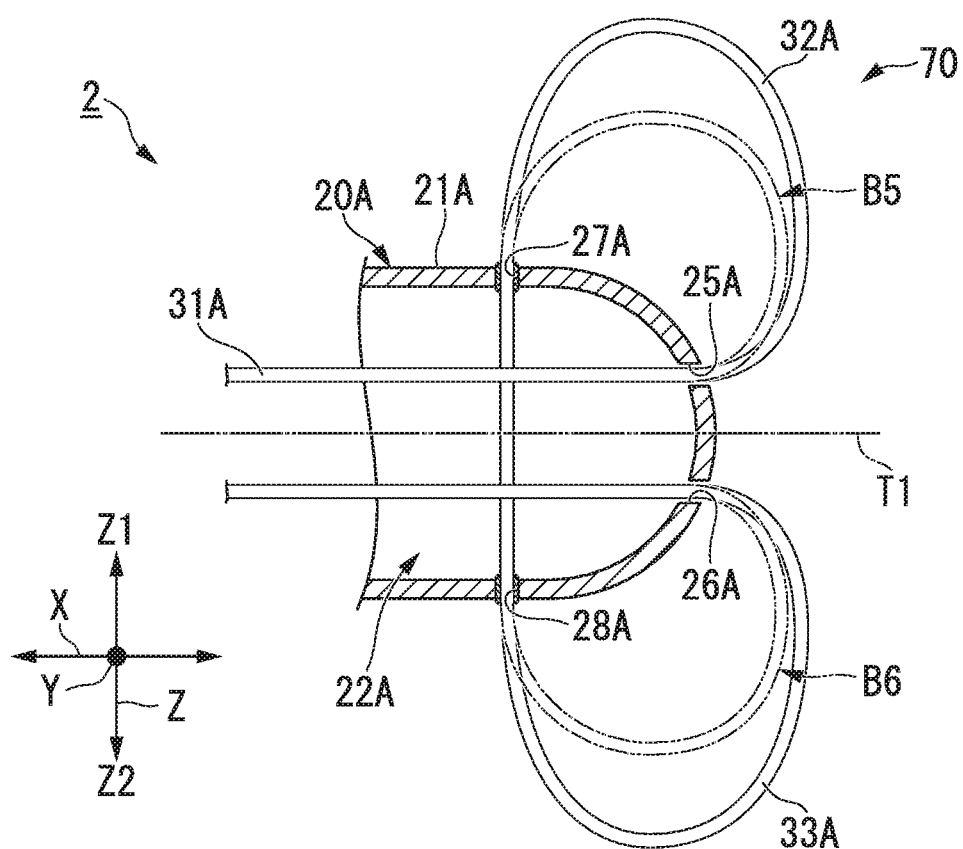
FIG. 20 is a cross-sectional view along the X-Z plane which describes a state in which both loop portions of the first actuating member protrude.

In the tissue grasping device 2 of the present embodiment configured in this manner, when the advancing and retracting manipulation wire 36A is pushed, as shown in FIG. 20, the first wire 31A further protrudes from the through-holes 25A and 26A. When the first wire 31A is fixed at a position of the through-hole 27A, the first loop portion 32A further protrudes mainly in the first orientation Z1 along the third axis Z with respect to the above-described loop shape B5. Similarly to the first loop portion 32A, when the advancing and retracting manipulation wire 36A is pushed, the third loop portion 33A further protrudes in the second orientation Z2 along the third axis Z with respect to the above-described loop shape B6.

According to the tissue grasping device 2 of the present embodiment, it is possible to collect a great amount of the necrotic tissues P6 at one time.

Figure 21:
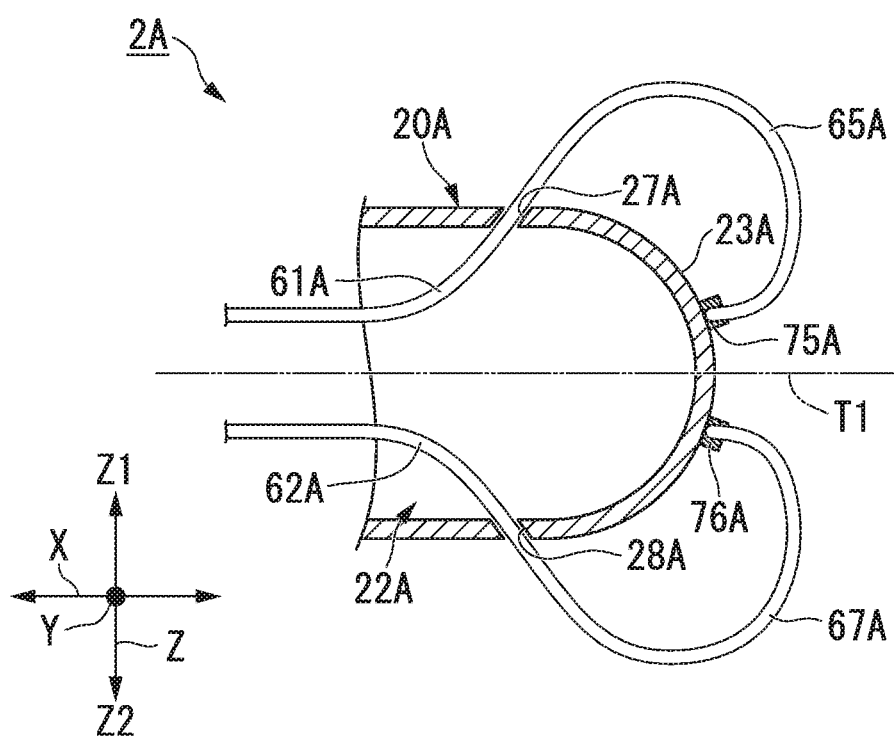
FIG. 21 is a cross-sectional view along the X-Z plane of a first actuating member in a modified example of the tissue grasping device of the second embodiment of the present invention.

In the present embodiment, like a tissue grasping device 2A shown in FIG. 21, the above-described wires 61A and 62A may be used in place of the first wire 31A without forming the through-holes 25A and 26A in the first actuating member 20A.

In this modified example, the through-holes 27A and 28A are formed to be farther from the reference plane T1 toward the distal end side. The first wire 61A that has passed through the internal space 22A is fixed to the distal end surface 23A of the first actuating member 20A by a fixing member 75A after it exits to the outside of the first actuating member 20A through the through-hole 27A. The third wire 62A that has passed through the internal space 22A is fixed to the distal end surface 23A of the first actuating member 20A by a fixing member 76A after it exits to the outside of the first actuating member 20A through the through-hole 28A. The through-hole 27A and the fixing member 75A are provided in the first orientation Z1 along the third axis Z with respect to the reference plane T1. The through-hole 28A and the fixing member 76A are provided in the second orientation Z2 along the third axis Z with respect to the reference plane T1.

According to the tissue grasping device 2A of the modified example configured in this manner, it is possible to obtain the same effects as in the tissue grasping device 2 of the present embodiment.

Third Embodiment

Next, a third embodiment of the present invention will be described with reference to FIG. 22 and FIG. 23. The same components as in the above embodiments are denoted with the same reference numerals, descriptions thereof will be omitted, and only different points will be described.

Figure 22:
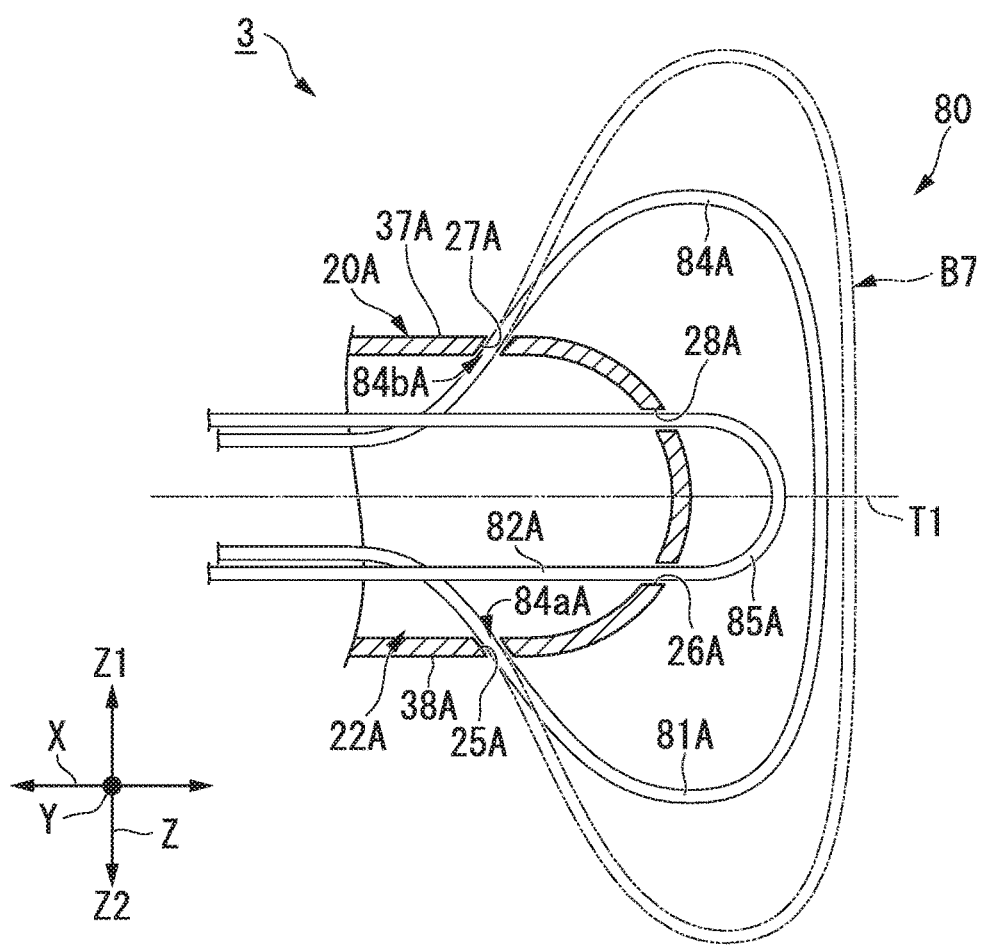
FIG. 22 is a cross-sectional view along the X-Z plane of a first actuating member in a tissue grasping device of a third embodiment of the present invention.

As shown in FIG. 22, a tissue grasping device 3 of the present embodiment includes a treatment portion 80 in place of the treatment portion 10 of the first embodiment. In the treatment portion 80, the through-holes 25A to 28A formed in the first actuating member 20A are disposed differently from those of the treatment portion 10. The through-hole 25A and the through-hole 27A from which a first wire (a wire member) 81A protrudes from the first actuating member 20A are positioned at the same along the first axis X and at more proximal side than the distal end of the first actuating member 20A. The through-hole 26A and the through-hole 28A from which a third wire (a wire member) 82A protrudes from the first actuating member 20A are positioned at the same along the first axis X. The through-holes 26A and 28A are disposed at more distal side than the through-holes 25A and 27A. In this example, the through-holes 26A and 28A extend along the first axis X. The through-holes 25A and 27A are formed to be farther away from the reference plane T1 toward the distal end side.

The first wire 81A that has passed through the internal space 22A forms a first loop portion 84A between a point existing to the outside of the first actuating member 20A through the through-hole 25A and a point returning to the internal space 22A through the through-hole 27A. The through-hole 25A restricts an extending direction of a first end portion 84aAA of the first loop portion 84A in the direction that intersects the outer side surface 38A of the first actuating member 20A. The through-hole 27A restricts an extending direction of a second end portion 84bA of the first loop portion 84A in the direction that intersects the outer side surface 37A of the first actuating member 20A. Similarly, the third wire 82A that has passed through the internal space 22A forms a third loop portion 85A between a point existing to the outside of the first actuating member 20A through the through-hole 26A and a point returning to the internal space 22A through the through-hole 28A. The first loop portion 84A is formed to surround the third loop portion 85A. A pair of end portions of the first wire 81A and a pair of end portions of the third wire 82A are connected to the distal end portion of the advancing and retracting manipulation wire 36A.

Figure 23:
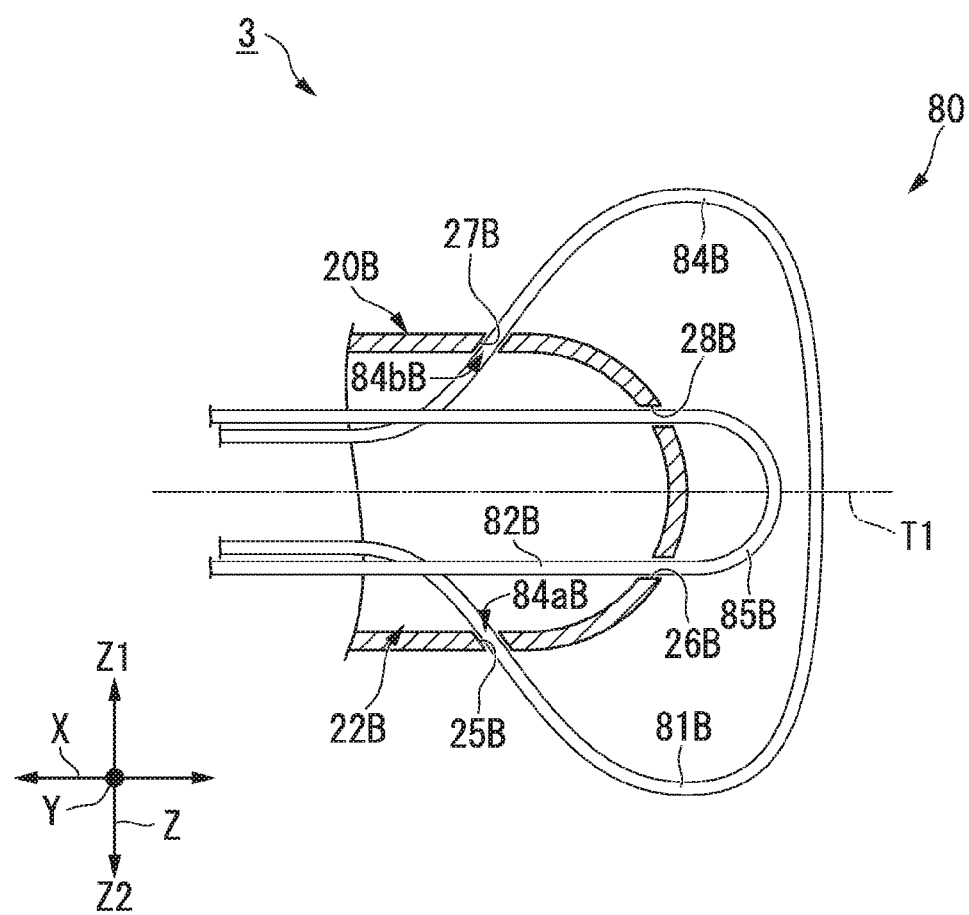
FIG. 23 is a cross-sectional view along the X-Z plane of a second actuating member in the tissue grasping device.

As shown in FIG. 23, the through-hole 25B and the through-hole 27B from which a second wire (a wire member) 81B protrudes from the second actuating member 20B are positioned at the same along the first axis X and at more proximal side than the distal end of the second actuating member 20B. The through-hole 26B and the through-hole 28B from which a fourth wire (a wire member) 82B protrudes from the second actuating member 20B are positioned at the same along the first axis X. The through-holes 26B and 28B are disposed at more distal side than the through-holes 25B and 27B.

The second wire 81B that has passed through the internal space 22B forms a second loop portion 84B between a point existing to the outside of the second actuating member 20B through the through-hole 25B and a point returning to the internal space 22B through the through-hole 27B. Similarly, the fourth wire 82B that has passed through the internal space 22B forms a fourth loop portion 85B between a point existing to the outside of the second actuating member 20B through the through-hole 26B and a point returning to the internal space 22B through the through-hole 28B. A pair of end portions of the second wire 81B and a pair of end portions of the fourth wire 82B are connected to the distal end portion of the advancing and retracting manipulation wire 36B.

In the tissue grasping device 3 of the present embodiment configured in this manner, when the advancing and retracting manipulation wire 36A is manipulated, the first loop portion 84A and the third loop portion 85A project from and are retracted to the first actuating member 20A. For example, when the advancing and retracting manipulation wire 36A is pushed, the first loop portion 84A becomes longer along the third axis Z in a loop shape B7 in FIG. 22. Similarly, when the advancing and retracting manipulation wire 36B is manipulated, the second loop portion 84B and the fourth loop portion 85B project from and are retracted to the second actuating member 20B.

According to the tissue grasping device 3 of the present embodiment, it is possible to collect a great amount of the necrotic tissues P6 at one time. In the present embodiment, the third loop portion 85A may not be formed in the first actuating member 20A. This is because it is possible to grasp the necrotic tissues P6 at the distal end side of the first actuating member 20A in addition to the first loop portion 84A. Similarly, the fourth loop portion 85B may not be formed in the second actuating member 20B.

Fourth Embodiment

Next, a fourth embodiment of the present invention will be described with reference to FIG. 24 to FIG. 29. The same components as in the above embodiment are denoted with the same reference numerals, descriptions thereof will be omitted, and only different points will be described.

Figure 24:
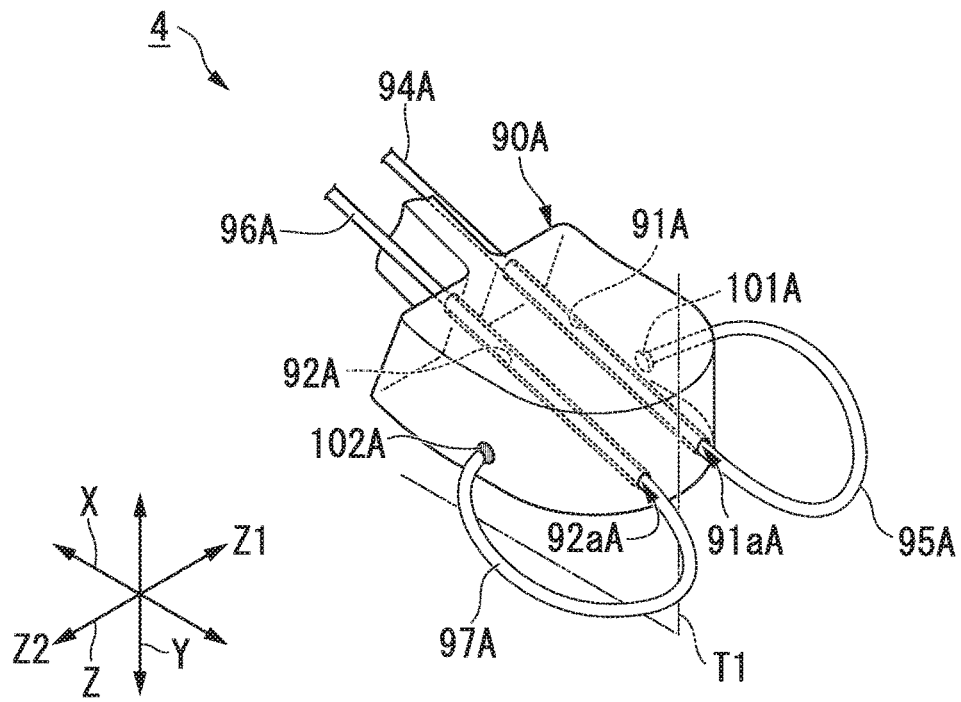
FIG. 24 is a perspective view of a first actuating member in a tissue grasping device of a fourth embodiment of the present invention.
Figure 25:
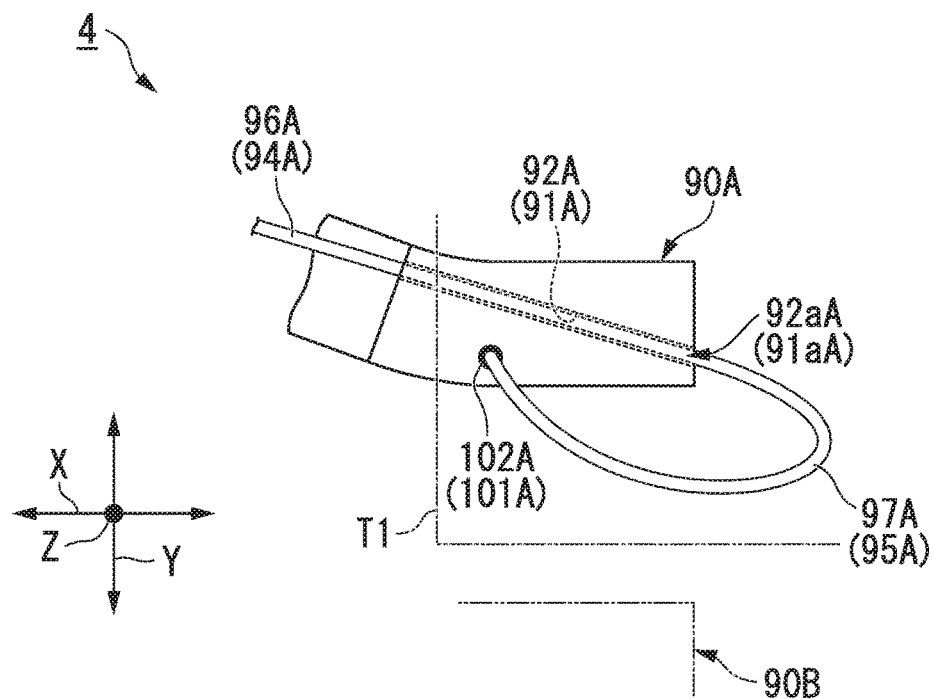
FIG. 25 is a side view of the first actuating member.
Figure 26:
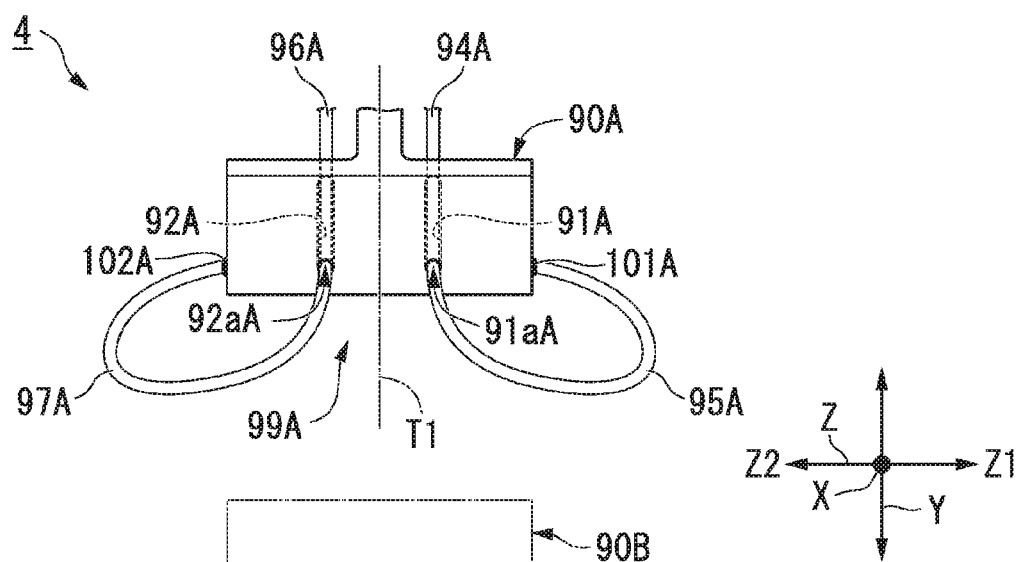
FIG. 26 is a front view of the first actuating member.

As shown in FIG. 24 to FIG. 26, in the first actuating member 90A included in a tissue grasping device 4 of the present embodiment, through-holes 91A and 92A are formed in parallel with the reference plane T1. When the first actuating member 90A and the second actuating member 90B are both in a closed state, the through-holes 91A and 92A are formed to approach the second actuating member 90B toward the distal end side.

A first wire (a wire member) 94A that is inserted into the through-hole 91A and protrudes toward the distal side is bent in the first orientation Z1 along the third axis Z and is bent to the proximal side, and the first wire 94A is fixed to the first actuating member 90A by a fixing member (a first restricting portion) 101A provided at more proximal side than an opening 91aA of the distal end of the through-hole 91A. When the actuating members 90A and 90B are in a closed state, the opening 91aA and the fixing member 101A have positions that are the same in a direction along the second axis Y (refer to FIG. 25). A portion of the first wire 94A between a point at which the first wire 94A which is inserted into the through-hole 91A is protruded toward the distal side and a point where is fixed to the first actuating member 90A forms a first loop portion 95A. When the through-hole 91A is formed as described above, a first wire 94A that protrudes toward the distal side through the through-hole 91A is curved in the first orientation Z1 along the third axis Z as it approaches the second actuating member 90B.

Similarly, a third wire (a wire member) 96A that is inserted into the through-hole 92A and protrudes toward the distal side is bent in the second orientation Z2 along the third axis Z and is bent to the proximal side, and the third wire 96A is fixed to the first actuating member 90A by a fixing member 102A provided at more proximal side than an opening 92aA of the distal end of the through-hole 92A. A portion of the third wire 96A between a point at which the third wire 96A which is inserted into the through-hole 92A is protruded toward the distal side and a point where is fixed to the first actuating member 90A forms a third loop portion 97A. When the through-hole 92A is formed as described above, the third wire 96A that protrudes toward the distal side through the through-hole 92A is curved in the second orientation Z2 along the third axis Z as it approaches the second actuating member 90B.

When viewed along the first axis X shown in FIG. 26, due to the wires 94A and 96A are curved as described above, the loop portions 95A and 97A are formed in a C shape having a concave portion 99A at the second actuating member 90B side as a whole. Although not shown, the loop portion of the second actuating member 90B configured in the same manner is also formed in a C shape having a concave portion at the first actuating member 90A as a whole. Accordingly, since the necrotic tissues P6 are surrounded by the loop portion when the actuating members 90A and 90B are in a closed state, the necrotic tissues P6 grasped by the loop portion are less likely to fall out along the third axis Z.

Figure 27:
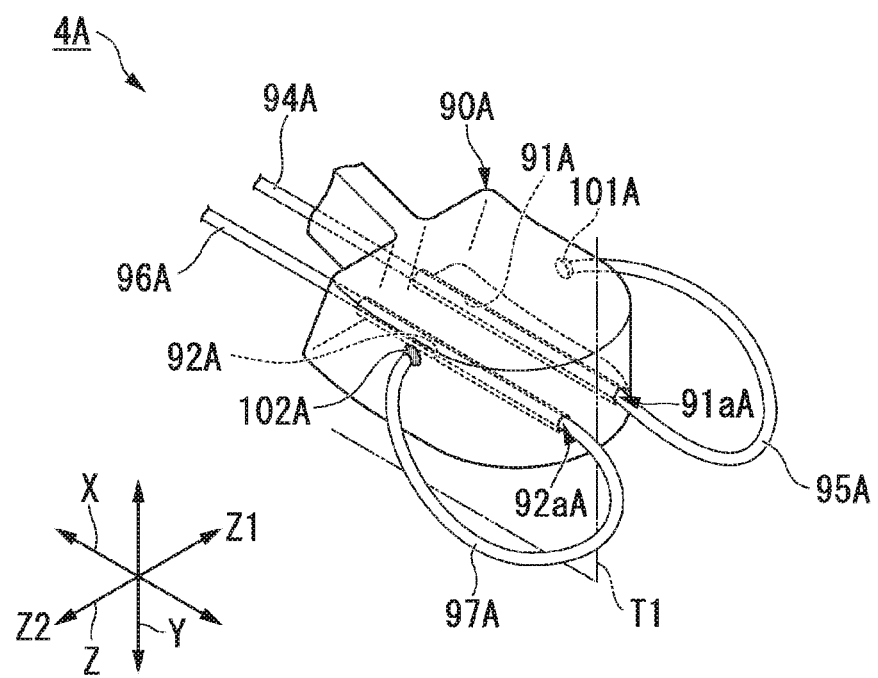
FIG. 27 is a perspective view of a first actuating member in a tissue grasping device in a modified example of the fourth embodiment of the present invention.
Figure 28:
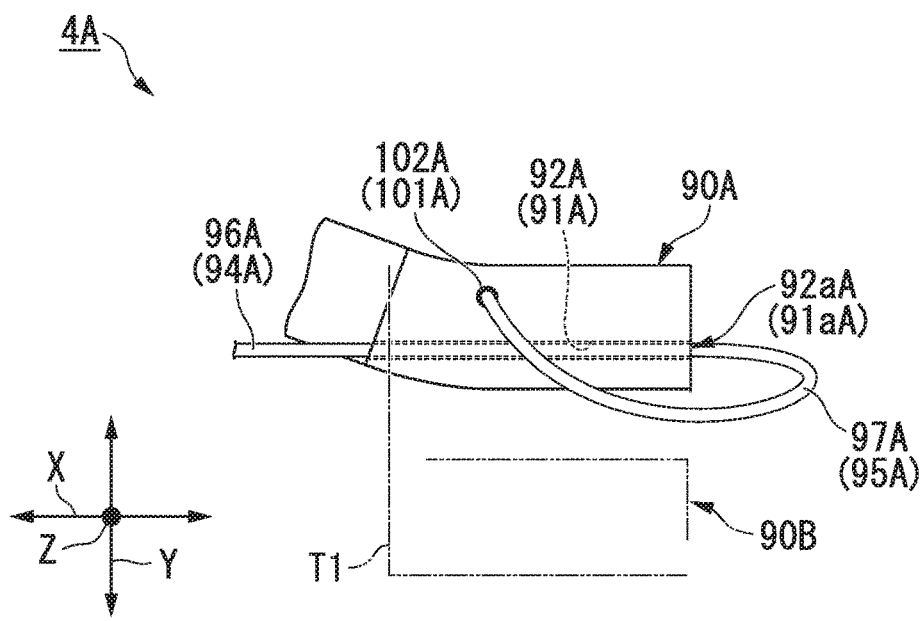
FIG. 28 is a side view of the first actuating member.
Figure 29:
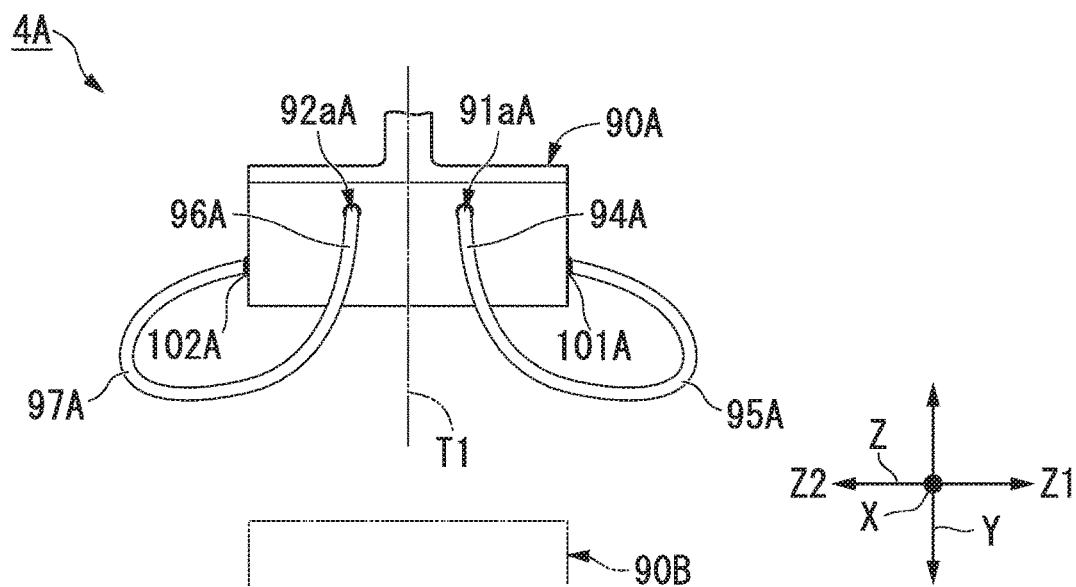
FIG. 29 is a front view of the first actuating member.

In the present embodiment, like a tissue grasping device 4A shown in FIGS. 27 to 29, in the tissue grasping device 4 of the fourth embodiment, the through-holes 91A and 92A may be formed to be parallel to the first axis X when the first actuating member 90A is in a closed state. In this modified example, when the actuating members 90A and 90B are in a closed state, the fixing member 101A is positioned farther from the second actuating member 90B than the opening 91aA (refer to FIG. 28). When the opening 91aA and the fixing member 101A are disposed as described above, the first wire 94A that protrudes toward the distal side through the through-hole 91A is curved as it approaches the second actuating member 90B toward the first orientation Z1 along the third axis Z. Similarly, the third wire 96A that protrudes toward the distal side through the through-hole 92A is curved as it approaches the second actuating member 90B toward the second orientation Z2 along the third axis Z.

In the tissue grasping device 4A of the present modified example, when viewed along the first axis X shown in FIG. 29, the loop portions 95A and 97A are formed in a C shape as a whole. Accordingly, when the actuating members 90A and 90B are in a closed state, the necrotic tissues P6 grasped by the loop portion are less likely to fall out along the third axis Z.

While the first embodiment to the fourth embodiment of the present invention have been described above with reference to the drawings, a specific configuration is not limited to the embodiments, but includes changes, combinations and omissions of the configuration in the range not departing from the spirit and scope of the present invention. Further, it is needless to say that configurations shown in the embodiments can be appropriately used in combination.

For example, while the through-holes 25A and 26A extend along the first axis X in the first embodiment and the second embodiment, the through-holes 25A and 26A may obliquely extend with respect to the first axis X. The through-holes 27A and 28A may also obliquely extend with respect to the first axis X. An orientation of the through-holes 25A, 26A, 27A, and 28A of the third embodiment is not particularly limited as long as the through-holes 25A and 26A are in parallel with the first axis X.

In the first embodiment to the fourth embodiment, two loop portions are formed in each of the actuating members 20A and 20B. However, the number of loop portions formed in the actuating members 20A and 20B is not limited thereto, and one loop portion or three or more loop portions may be provided. In addition, the numbers of loop portions formed in the actuating members 20A and 20B may be different from each other.

The present invention is not limited to the above descriptions, but is only limited by the range of appended claims.

What is claimed is:

1. A tissue grasping device comprising:
    a longitudinal axis member configured to be inserted into a body;
    first and second actuating members provided at a distal end portion of the longitudinal axis member, the second actuating member being movable in a direction toward the first actuating member from a position spaced apart from the first actuating member; and
    first and second wire members that extend to an outside of the first and second actuating members, respectively, wherein:
    the first wire member comprises:
        a first loop portion that is curved in a loop shape outside of the first actuating member between a distal surface of the first actuating member and a first outer side surface of the first actuating member proximal to the distal surface;
        a first distal portion that extends through a first distal through-hole in the distal surface of the first actuating member; and
        a first proximal portion that extends through a first side through-hole in the first outer side surface of the first actuating member; and the second wire member comprises:
 a second loop portion that is curved in a loop shape outside of the second actuating member between a distal surface of the second actuating member and a second outer side surface of the second actuating member proximal to the distal surface;
 a second distal portion that extends through a second distal through-hole in the distal surface of the second actuating member; and
 a second proximal portion that extends through a second side through-hole in the second outer side surface of the second actuating member.

2. The tissue grasping device according to claim 1, wherein:
 the first proximal portion of the first wire is fixed to the first actuating member within the first side through-hole; and
 the second proximal portion of the second wire is fixed to the second actuating member within the second side through-hole.

3. The tissue grasping device according to claim 1, wherein:
 the first actuating member includes a first cavity, and the first distal through-hole and the first side through-hole communicate with the first cavity; and
 the second actuating member includes a second cavity, and the second distal through-hole and the second side through-hole communicate with the second cavity.

4. The tissue grasping device according to claim 1, wherein:
 the first wire member further comprises a third loop portion that is curved in a loop shape outside of the first actuating member between the distal surface of the first actuating member and a third outer side surface of the first actuating member proximal to the distal surface; and
 the second wire member further comprises a fourth loop portion that is curved in a loop shape outside of the second actuating member between the distal surface of the second actuating member and a fourth outer side surface of the second actuating member proximal to the distal surface.

5. The tissue grasping device according to claim 4, wherein:
 the first and third loop portions of the first wire member intersect with each other outside of the first actuating member; and
 the second and fourth loop portions of the second wire member intersect with each other outside of the second actuating member.

6. The tissue grasping device according to claim 4, wherein:
 the first and third loop portions of the first wire member do not intersect with each other outside of the first actuating member; and
 the second and fourth loop portions of the second wire member do not intersect with each other outside of the second actuating member.

7. A tissue grasping device comprising:
 a longitudinal axis member configured to be inserted into a body;
 first and second actuating members provided at a distal end portion of the longitudinal axis member, the second actuating member being movable in a direction toward the first actuating member from a position spaced apart from the first actuating member; and first and second wire members that extend to an outside of the first and second actuating members, respectively, wherein:
 the first wire member comprises:
  a first loop portion that is curved in a loop shape outside of the first actuating member between a distal surface of the first actuating member and a first outer side surface of the first actuating member proximal to the distal surface;
  a first distal portion that extends through a first distal through-hole in the distal surface of the first actuating member; and
  a first proximal portion that is fixed to the first outer side surface of the first actuating member; and
 the second wire member comprises:
  a second loop portion that is curved in a loop shape outside of the second actuating member between a distal surface of the second actuating member and a second outer side surface of the second actuating member proximal to the distal surface;
  a second distal portion that extends through a second distal through-hole in the distal surface of the second actuating member; and
  a second proximal portion that is fixed to the second outer side surface of the second actuating member.

8. The tissue grasping device according to claim 7, wherein:
 the first proximal portion of the first wire is fixed to the first outer side surface of the first actuating member by a first fixing member; and
 the second proximal portion of the second wire is fixed to the second outer side surface of the second actuating member by a second fixing member.

9. The tissue grasping device according to claim 8, wherein:
 the first proximal portion of the first wire is fixed to the first outer side surface of the first actuating member by the first fixing member at a position between a distal end of the first actuating member and a proximal end of the first actuating member; and
 the second proximal portion of the second wire is fixed to the second outer side surface of the second actuating member by the second fixing member at a position between a distal end of the second actuating member and a proximal end of the second actuating member.

10. The tissue grasping device according to claim 7, further comprising:
 third and fourth wire members that extend to an outside of the first and second actuating members, respectively, wherein:
 the third wire member comprises:
  a third loop portion that is curved in a loop shape outside of the first actuating member between the distal surface of the first actuating member and a third outer side surface of the first actuating member that is proximal to the distal surface and facing an opposite direction of the first outer side surface of the first actuating member;
  a third distal portion that extends through a third distal through-hole in the distal surface of the first actuating member; and
  a third proximal portion that is fixed to the third outer side surface of the first actuating member;
 the fourth wire member comprises:
  a fourth loop portion that is curved in a loop shape outside of the second actuating member between the distal surface of the second actuating member and a fourth outer side surface of the second actuating member that is proximal to the distal surface and facing an opposite direction of the second outer side surface of the second actuating member;
a fourth distal portion that extends through a fourth distal through-hole in the distal surface of the second actuating member; and
a fourth proximal portion that is fixed to the fourth outer side surface of the second actuating member;
internal portions of the first and third wires extend within the first actuating member from a distal end of the first actuating member to a proximal end of the first actuating member; and
internal portions of the second and fourth wires extend within the second actuating member from a distal end of the second actuating member to a proximal end of the second actuating member.

11. The tissue grasping device according to claim 10, wherein:
the first and third loop portions of the first and third wire members do not intersect with each other outside of the first actuating member; and
the second and fourth loop portions of the second and fourth wire members do not intersect with each other outside of the second actuating member.

12. A tissue grasping device comprising:
a longitudinal axis member configured to be inserted into a body;
first and second actuating members provided at a distal end portion of the longitudinal axis member, the second actuating member being movable in a direction toward the first actuating member from a position spaced apart from the first actuating member; and
first and second wire members that extend to an outside of the first actuating member and the second actuating member, respectively,
wherein:
the first wire member comprises:
a first loop portion that is curved in a loop shape outside of the first actuating member between a distal surface of the first actuating member and a first outer side surface of the first actuating member proximal to the distal surface;
a first distal portion that is fixed to the distal surface of the first actuating member; and
a first proximal portion that extends through a first side through-hole in the first outer side surface of the first actuating member; and
the second wire member comprises:
a second loop portion that is curved in a loop shape outside of the second actuating member between a distal surface of the second actuating member and a second outer side surface of the second actuating member proximal to the distal surface;
a second distal portion that is fixed to the distal surface of the second actuating member; and
a second proximal portion that extends through a second side through-hole in the second outer side surface of the first actuating member.

13. The tissue grasping device according to claim 12, wherein:
the first distal portion of the first wire is fixed to the distal surface of the first actuating member by a first fixing member; and
the second distal portion of the second wire is fixed to the distal surface of the second actuating member by a second fixing member.

14. The tissue grasping device according to claim 12, further comprising:
a third wire member that extends to an outside of the first actuating member and comprises a third loop portion that is curved in a loop shape outside of the first actuating member; and
a fourth wire member that extends to an outside of the second actuating member and comprises a fourth loop portion that is curved in a loop shape outside of the second actuating member.

\* \* \* \* \*